(12) United States Patent
Silva Guisasola et al.

(10) Patent No.: US 10,626,080 B2
(45) Date of Patent: Apr. 21, 2020

(54) PROCESS FOR THE PREPARATION OF BIMATOPROST

(71) Applicant: GENTEC, S.A., Barcelona (ES)

(72) Inventors: Luis Octavio Silva Guisasola, Aldemayor de San Martín (ES); Joaquín Nebot Troyano, Avinyonet del Penedés (ES); Jordi Ripoll Altadill, Avinyonet del Penedés (ES)

(73) Assignee: GENTEC, S.A., Barcelona (ES)

(*) Notice: Subject to any disclaimer, the term of this patent is extended or adjusted under 35 U.S.C. 154(b) by 30 days.

(21) Appl. No.: 16/090,572

(22) PCT Filed: Apr. 18, 2017

(86) PCT No.: PCT/EP2017/059180
§ 371 (c)(1),
(2) Date: Oct. 1, 2018

(87) PCT Pub. No.: WO2017/182465
PCT Pub. Date: Oct. 26, 2017

(65) Prior Publication Data
US 2020/0010406 A1 Jan. 9, 2020

(30) Foreign Application Priority Data
Apr. 19, 2016 (EP) .................................. 16382174

(51) Int. Cl.
C07C 231/14 (2006.01)
C07C 233/10 (2006.01)
C07C 69/608 (2006.01)
C07C 67/04 (2006.01)

(52) U.S. Cl.
CPC ............ C07C 231/14 (2013.01); C07C 67/04 (2013.01); C07C 69/608 (2013.01); C07C 233/10 (2013.01)

(58) Field of Classification Search
CPC ... C07C 231/14; C07C 233/10; C07C 69/608; C07C 67/04
USPC ......................................................... 560/55
See application file for complete search history.

(56) References Cited

FOREIGN PATENT DOCUMENTS

| WO | WO9406433 | 3/1994 | |
|---|---|---|---|
| WO | WO2002024639 | 3/2002 | |
| WO | WO02096868 | 12/2002 | |
| WO | WO2005058812 | 6/2005 | |
| WO | WO-2005058812 A2 * | 6/2005 | ........... C07C 405/00 |
| WO | WO2010109476 | 9/2010 | |

OTHER PUBLICATIONS

International Search Report and Written Opinion dated Jun. 21, 2017 for PCT Application No. PCT/EP2017/059180, 13 pages.

* cited by examiner

Primary Examiner — Deborah D Carr
(74) Attorney, Agent, or Firm — Squire Patton Boggs (US) LLP

(57) ABSTRACT

It is provided a process for the preparation of bimatoprost, which comprises: a) reacting a compound of formula (III) with ethylamine in the presence of a suitable solvent; and b) deprotecting compound obtained in step a) to obtain bimatoprost, wherein $R^1$ is selected from $(C_1-C_{16})$alkyl, $(C_1C_{16})$haloalkyl, $(C_2-C_{16})$alkenyl, $(C_2-C_{16})$haloalkenyl, $(C_1-C_{16})$alkoxy$(C_1-C_{16})$alkyl, aryl, $(C_1-C_{16})$alkylaryl, allyl, $-(CH_2-CH_2-O)_n-CH_3$ wherein n=1, 2, 3 or 4, and $-CH(O-CH_2-CH_2)_2$; $R_2$ is selected from H, $(C_1-C_{16})$alkyl, $(C_1-C_{16})$haloalkyl, $(C_2-C_{16})$alkenyl, $(C_2-C_{16})$haloalkenyl, $(C_1-C_{16})$alkoxy$(CrC_{16})$alkyl, aryl, $(C_1-C_{16})$alkylaryl, allyl; or, alternatively, $R^1$ and $R^2$ taken together are selected from $-CH_2-CH_2-CH_2-$, $-CH_2-CH_2-$, $-O-CH_2-CH_2-$, and $-O-CH=CH-$. There are also provided intermediates useful in such preparation process.

(III)

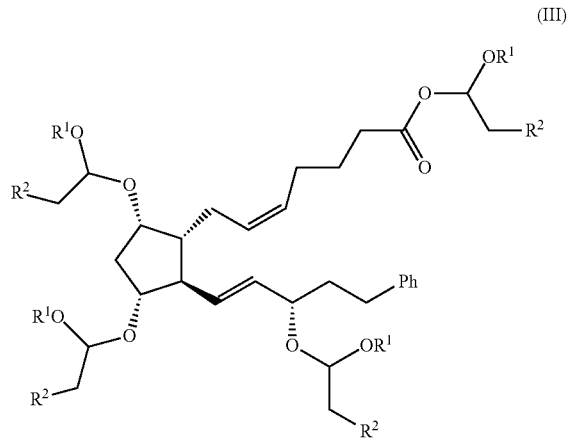

20 Claims, No Drawings

PROCESS FOR THE PREPARATION OF BIMATOPROST

This application claims the benefit of European Patent Application EP16382174.7 filed on Apr. 19, 2016.

TECHNICAL FIELD

The present invention relates to a process for the preparation of bimatoprost, as well as to some new intermediates useful in such preparation process.

BACKGROUND ART

Bimatoprost is the generic name of compound (Z)-7-[(1R,2R,3R,5S)-3,5-dihydroxy-2-[(E,3S)-3-hydroxy-5-phenylpent-1-enyl]cyclopentyl]-N-ethylhept-5-enamide, the chemical structure of which is the following:

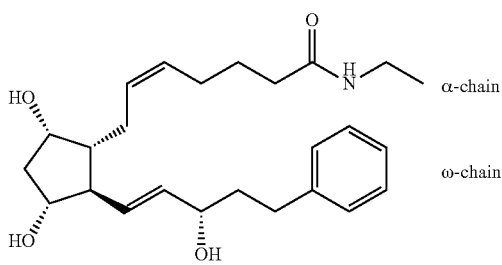

Bimatoprost is a prostaglandin derivative of the PGF2α-series used topically (as eye drops) to control the progression of glaucoma and in the management of ocular hypertension.

Bimatoprost was first disclosed in document WO199406433. This document, as well as later documents such as WO2002096868 and WO20100109476, discloses processes for the preparation of bimatoprost wherein in the last step of the synthesis the amide moiety is formed via a methyl ester intermediate by reaction with ethylamine. The methyl ester intermediate is previously obtained by reaction of the corresponding carboxylic acid with IMe. The reaction is carried out either with the hydroxyl groups of the molecule unprotected or protected in part. The use of IMe is not advisable as it is considered to be a human carcinogen. Additionally, the reaction of the methyl ester with ethylamine to obtain the ethylamide derivative takes place at a very low speed and with the formation of the corresponding carboxylic acid as side-product in a significant amount.

WO2005058812 discloses a process for the preparation of bimatoprost from a tripotected precursor having a free carboxylic acid group. The amidation reaction is carried out either with ethylamine in the presence of a carbodiimide or with previous esterification (formation of the methyl ester as mentioned above) of the corresponding acid precursor. Nevertheless, overall yields reported are very low.

A variety of methods synthesising bimatoprost or other PGFα prostaglandins analogues have been disclosed following several alternatives. In general, the ones wherein the α-chain is introduced using the Wittig reagent 4-(carboxybutyl)triphenylphosphonium bromide to give the corresponding acid which has to be converted into an amide to obtain bimatoprost require the use of elaborated protecting group strategies. As an alternative to the formation of an ester previously to the amidation reaction, the acid is activated by groups other than an ester. Nevertheless, these alternative processes require the use of reactants that either are toxic or generate toxic waste, what is a drawback for the production on an industrial scale. Additionally, bimatoprost is obtained in insufficient purity.

In view of the processes disclosed in the prior art, particularly the ones disclosed herein above, and the problems associated therewith, it is an object of the present invention to provide an alternative process for the synthesis of bimatoprost.

SUMMARY OF THE INVENTION

Inventors have found a new process for the preparation of bimatoprost that overcomes and/or minimizes some of the drawbacks of the processes disclosed in the prior art. The new process allows obtaining bimatoprost with unexpectedly high overall yields and high purity. The process is easy to scale-up to an industrial level, and is more cost-effective than the already known processes.

Accordingly, a first aspect of the present invention refers to a process for the preparation of a compound of formula (I)

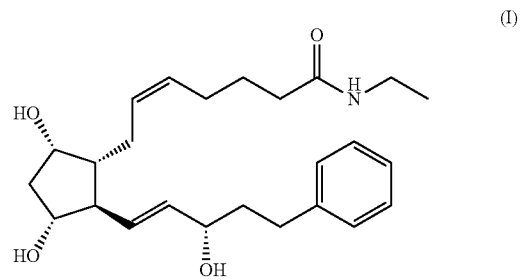 [SMILES: CCNC(=O)CCC/C=C\C[C@@H]1[C@@H](/C=C/[C@@H](O)CCc2ccccc2)[C@H](O)C[C@@H]1O]

which is bimatoprost, which comprises the following steps:

a) reacting a compound of formula (III):

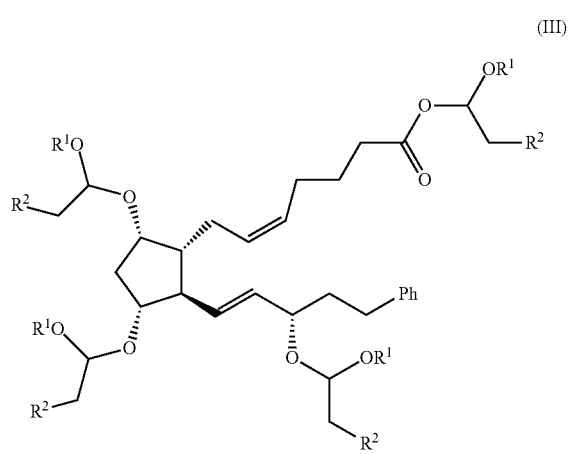

with ethylamine in the presence of a suitable solvent in order to obtain a compound of formula (II)

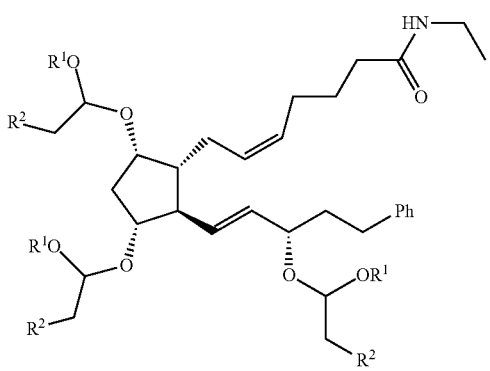

(II)

and b) deprotecting compound of formula (II) to yield bimatoprost, wherein $R^1$ is selected from the group consisting of $(C_1-C_{16})$alkyl such as methyl, ethyl, n-propyl, isopropyl, n-butyl, sec-butyl, isobutyl, tert-butyl, isoctyl, hexadecyl, and cyclohexyl; $(C_1-C_{16})$haloalkyl such as 2-chloroethyl, 2-trifluoroethyl, and pentafluoroethyl; $(C_2-C_{16})$alkenyl; $(C_2-C_{16})$haloalkenyl; $(C_1-C_{16})$alkoxy$(C_1-C_{16})$alkyl; aryl such as phenyl, bencyl, and biphenylmethyl; $(C_1-C_{16})$alkylaryl, allyl, —$(CH_2-CH_2-O)_n$—$CH_3$ wherein n=1, 2, 3 or 4, and —$CH(O-CH_2-CH_2)_2$, $R^2$ is selected from the group consisting of H, $(C_1-C_{16})$alkyl, $(C_1-C_{16})$haloalkyl, $(C_2-C_{16})$alkenyl, $(C_2-C_{16})$haloalkenyl, $(C_1-C_{16})$alkoxy$(C_1-C_{16})$alkyl, aryl, $(C_1-C_{16})$alkylaryl, allyl, or, alternatively, $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—, that is, $R^1$ and $R^2$ taken together with the atoms to which they are joined form a 5 or 6 membered heterocycle having the formula:

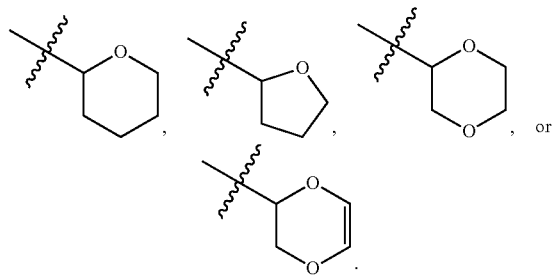

Surprisingly, inventors have found that the process of the invention allows obtaining bimatoprost with overall yields unexpectedly higher than the ones obtained by the processes known in the prior art, and at the same time with a high purity, as can be seen from the Examples compared to Comparative Example. Particularly, the presence on intermediate compound of formula (III) of an ester group on an acetalic carbon provides to this intermediate an improved reactivity compared to other esters, such as methylic ester. Thus, the amidation reaction is faster and the generation of the acid derivative as a side-product is significantly decreased. Additionally, the fact that all the hydroxilic groups are protected also decreases the generation of other in the amidation step. All this results in the global process being more cost-effective.

According to a second aspect of the invention, new compounds of formula (III)

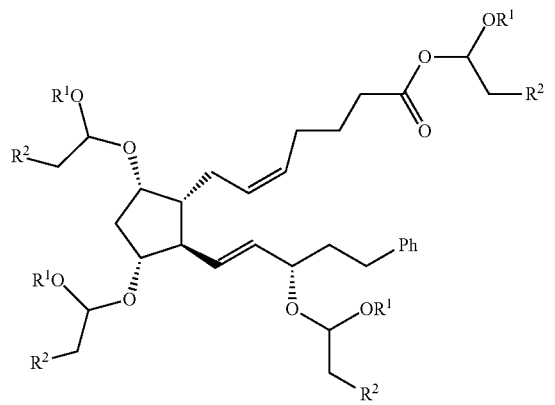

wherein $R^1$ and $R^2$ are as defined above, and of formula (II)

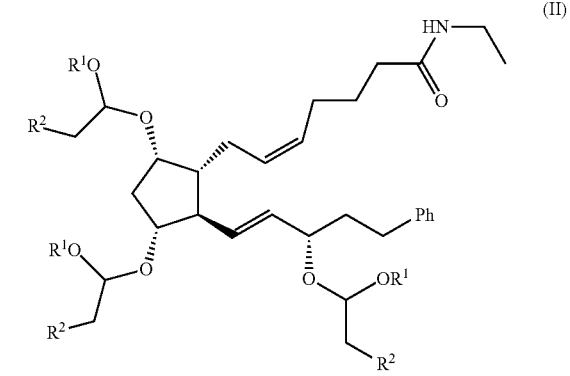

wherein $R^1$ and $R^2$ are as defined above or, alternatively, $R^1$ and $R^2$ taken together are selected from the group consisting of —$CH_2$—$CH_2$—, —O—$CH_2$—$CH_2$—, and —O—CH=CH—, are provided as intermediates useful for the preparation of bimatoprost.

Another aspect of the invention relates to a process for the preparation of the compound of formula (III) as defined above, the process comprising reacting a compound of formula (V) with a vinyl ether of formula (IV)

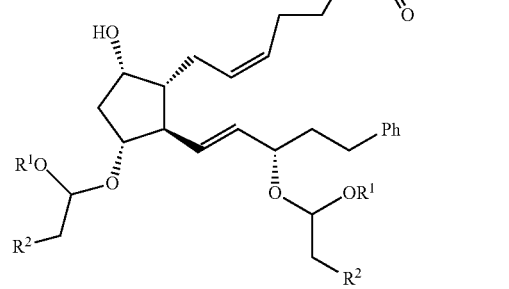

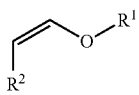

(IV)

wherein $R^1$ and $R^2$ are as defined above or, alternatively, $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—, in the presence of an acid catalyst.

Advantageously and surprisingly, this reaction allows the protection of the remaining hydroxyl group on compound of formula (V) and, simultaneously, the esterification of the carboxylic group. As commented above, the presence of the ester group on an acetalic carbon provides intermediate compound of formula (III) with an improved reactivity compared to other esters.

Still another aspect of the invention relates to a process for the preparation of the compound of formula (II) as defined above, the process comprising reacting a compound of formula (III):

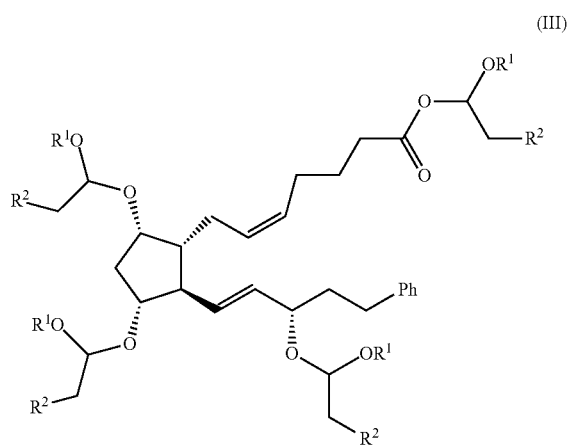

(III)

wherein $R^1$ and $R^2$ are as defined above or, alternatively, $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—, with ethylamine in the presence of a suitable solvent.

Compounds (II) and (III) allow the preparation of bimatoprost by a process which proceeds with high yields and purity. Therefore, it is also part of the invention the use of the compounds of formula (III) or (II) as intermediates for the preparation of bimatoprost.

DETAILED DESCRIPTION OF THE INVENTION

As used herein the term "alkyl" refers to includes straight or branched chain or cyclized hydrocarbyl radicals containing the number of carbon atoms specified in the description or claims. Thus, by way of example, the term "($C_1$-$C_4$)alkyl" refers to a saturated straight or branched hydrocarbon chain containing from 1 to 4 carbon atoms, in particular methyl, ethyl, propyl, isopropyl, n-butyl, isobutyl, sec-butyl, and tert-butyl.

As used herein the term "alkenyl" refers to an ethylenically unsaturated hydrocarbon group, straight or branched, having a chain length the number of carbon atoms specified in the description or claims and 1 to 2 ethylenic bonds.

As used herein the term "alkoxy" refers to both branched and straight chain alkyl groups containing the number of carbon atoms specified in the description or claims at least one oxygen atom. Typical alkoxy groups are methoxy, ethoxy, n-propoxy, isopropoxy, n-butoxy, sec-butoxy, isobutoxyl, t-butoxy, n-pentoxy, isopentoxy, n-hexoxy, n-heptoxy and the like.

The term "aryl" refers to a radical of one ring system with 1-3 rings, the rings being aromatic and being isolated or partially/totally fused and having 5-6 members, the ring system being optionally substituted by one or more radicals independently selected from the group consisting of ($C_1$-$C_6$)alkyl, ($C_1$-$C_6$)alkoxy, nitro, cyano, and halogen. Examples of aryl groups are phenil, bencyl, and biphenylmethyl As used herein the rings in the ring system being "isolated" embraces either only one ring or a ring system formed by two, three or four rings wherein said rings are bound to any one of the other rings through a bond.

As used herein the rings in the ring system being "totally fused" embraces a ring system formed by two, three or four rings in which two or more atoms are common to two adjoining rings. Illustrative non-limitative examples of fused aromatic ring systems are 1,2,3,4-tetrahydronaphthyl, 1-naphthyl, 2-naphthyl, anthryl, or phenanthryl, As used herein the rings in the ring system being "partially fused" embraces a ring system formed by three or four rings, being at least two of said rings totally fused and the remaining ring(s) or fused rings being bound through a bond from the atom of one ring or fused rings to the atom of another ring or fused rings.

As used herein the term "alkylaryl" refers to groups having an alkyl moiety containing the number of carbon atoms specified in the description or claims attached to an aryl ring. The alkyl moiety is preferably a straight, branched or cyclic alkyl group having 1 to 6 carbon atoms.

As used herein the term "alkoxyalkyl" refers to an alkoxy moiety covalently bonded to an alkyl moiety.

As mentioned above, bimatoprost can be prepared by reacting a compound of formula (III):

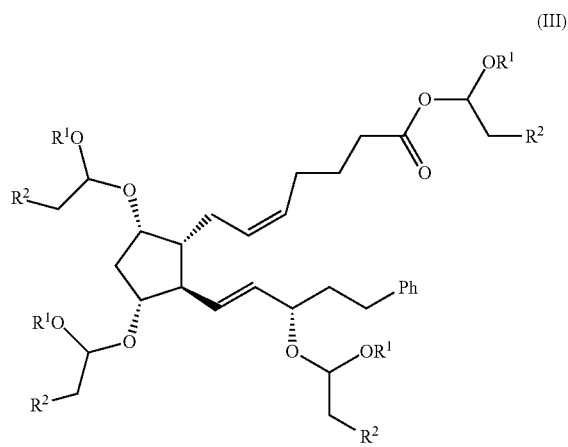

(III)

wherein $R^1$ and $R^2$ are as defined above or, alternatively, $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—; with ethylamine in order to obtain a compound of formula (II)

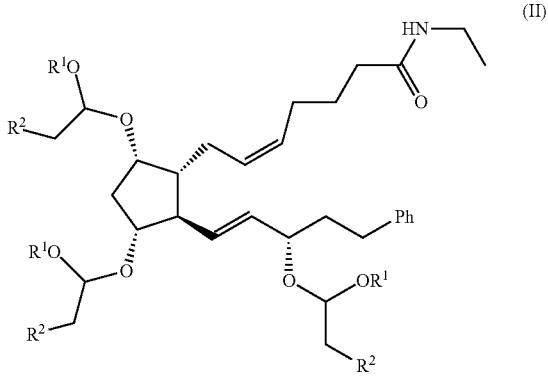

(II)

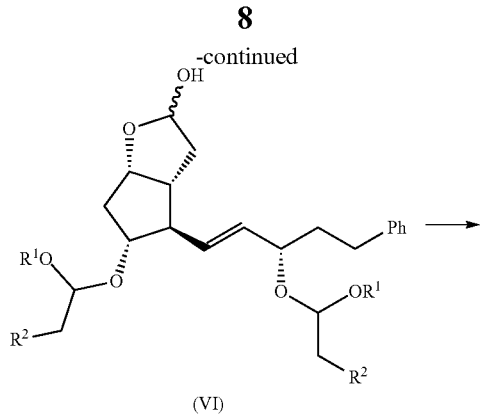

(VI)

wherein $R^1$ and $R^2$ are defined as above or, alternatively, $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—; submitting the obtained compound to a deprotection reaction.

In a particular embodiment of the process of the invention, $R^1$ is a ($C_1$-$C_4$)alkyl and $R^2$ is H. More particularly, $R^1$ is selected from ethyl and n-butyl and $R^2$ is H.

In another particular embodiment of the process of the invention, $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—. More particularly, $R^1$ and $R^2$ taken together are —$CH_2$—$CH_2$—$CH_2$—.

Scheme I below illustrates a particular embodiment of the general process of the invention:

Scheme I

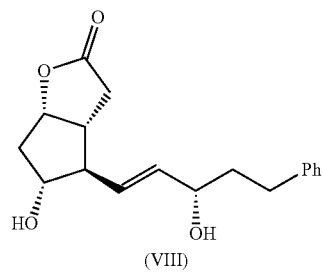

(VIII)

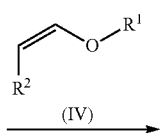

(IV)

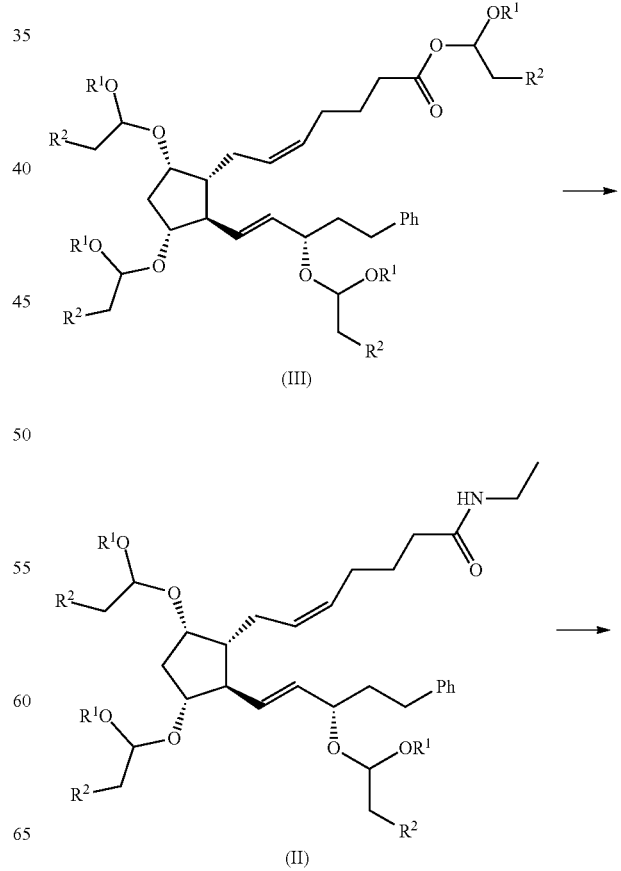

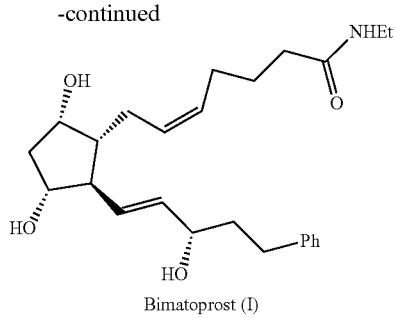

Bimatoprost (I)

Compound of formula (VIII), also known as bimatoprost lactone diol, is commercially available.

As illustrated in Scheme I, compound of formula (VII) can be prepared from compound of formula (VIII) by reaction with a vinyl ether of formula (IV)

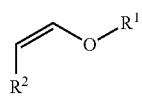

wherein $R^1$ and $R^2$ are as defined above or, alternatively, $R^1$ and $R^2$ taken together are selected from the group consisting of —CH$_2$—CH$_2$—CH$_2$—, —CH$_2$—CH$_2$—, —O—CH$_2$—CH$_2$—, and —O—CH=CH—, in the presence of an acid catalyst.

Examples of vinyl ethers of formula IV are, without being limited to, tetraethylene glycol methylvinyl ether, tri(ethylene glycol) methyl vinyl ether, diethylene glycol methyl vinyl ether, diethyl vinyl orthoformate, and cyclic vinyl ethers such as 3,4-dihydropyrane, 2,3-dihydrofurane, 1,4-dioxin, and 2,3-dihydro-1,4-dioxin.

Usually, the reaction is carried out with a molar ratio of the vinyl ether of formula (IV) from 2.0 moles per mol of compound of formula (VIII) to an amount wherein the vinyl ether itself acts as solvent, such as 5 volumes of vinyl ether per gram of compound of formula (VIII). Acid catalysis can be performed by any strong inorganic or organic acid and salts thereof with a weak base Examples of acid catalysts useful in the process of the invention include p-toluenesulfonic acid, methanesulfonic acid, pyridinium p-toluenesulfonate, and pyridinium methanesulfonate. The amount of catalyst can be from 0.1 to 1.0 moles of acid or its salt per each mol of compound of formula (VIII).

The reaction can be carried out in a suitable solvent, particularly in an anhydrous aprotic solvent such as halogenated hydrocarbons, aliphatic or aromatic hydrocarbons, ethers, dimethylformamide, dimethylacetamide, and dimethylsulfoxide. Preferred solvents are tetrahydrofuran, dichloromethane, and toluene. The reaction temperature can be from 0° C. y 100° C. depending on the solvent used.

The preparation of compound of formula (VI) can be accomplished by reduction of compound of formula (VII) with a suitable reducing agent in the presence of an aprotic solvent such as tetrahydrofuran (THF), 2-methyltetrahydrofuran (MeTHF), diethylether, disopropylether, toluene, halogenated hydrocarbides such as dichloromethane, dimethylacetamide (DMA), and dimethylformamide (DMF). Examples of a suitable reducing agent include diisoamylaluminium hydride, diisobutylaluminium hydride and sodium diethylaluminum hydride. More particularly, the reducing agent is diisobutylaluminium hydride.

Compound of formula (V) can be prepared by submitting compound of formula (VI) to a Wittig reaction with a (4-carboxybutyl)triphenylphosphonium halide, such as bromide or chloride, in the presence of a base and a suitable solvent. Examples of bases include butyl lithium, sodium amide, sodium hydride, sodium methoxide, sodium ethoxide, potassium tert-butoxide or potassium ethoxide, preferably potassium tert-butoxide is used. Examples of suitable solvent include tetrahydrofuran, toluene, dichloromethane, or mixtures thereof. Particularly, potassium tert-butoxide is used as a base and tetrahydrofuran as solvent.

Compound of formula (III) can be prepared from compound of formula (V) by reaction with a vinyl ether of formula (IV)

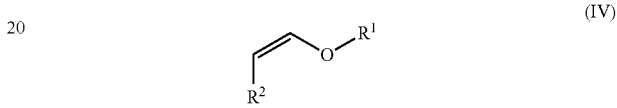

wherein $R^1$ and $R^2$ are as defined above or, alternatively, $R^1$ and $R^2$ taken together are selected from the group consisting of —CH$_2$—CH$_2$—CH$_2$—, —CH$_2$—CH$_2$—, —O—CH$_2$—CH$_2$—, and —O—CH=CH—, in the presence of an acid catalyst. The process is carried out similarly as for the preparation of compound of formula (VII) explained above, namely with a molar ratio of the vinyl ether of formula (IV) from 2.0 moles per mol of compound of formula (V) to an amount wherein the vinyl ether itself acts as solvent, such as 5 volumes of vinyl ether per gram of compound of formula (V). Acid catalysis can be performed by any strong inorganic or organic acid and salts thereof with a weak base such as p-toluenesulfonic acid, methanesulfonic acid, pyridinium p-toluenesulfonate, and pyridinium methanesulfonate. The amount of catalyst can be from 0.1 to 1.0 moles of acid or its salt per each mol of compound of formula (VIII). The reaction can be carried out in an anhydrous aprotic solvent such as halogenated hydrocarbons, aliphatic or aromatic hydrocarbons, ethers, dimethylformamide, dimethylacetamide, and dimethylsulfoxide. Preferred solvents are tetrahydrofurane, dichloromethane, and toluene. The reaction temperature can be from 0° C. y 100° C. depending on the solvent used.

In a particular embodiment, compound of formula (III) can be prepared from compound of formula (V) according to the following reaction conditions and reactants:
  0.2 moles of pyridinium p-toluenesulfonate per mol of compound of formula (V),
  11.0 moles of vinyl ether (such as butyl vinyl ether, ethyl vinyl ether or dihydropirane) per mol of compound of formula (V),
  5 ml of toluene per gram of compound of formula (V),
  at a temperature of 25±2° C. for about 3 hours.

The kinetics of the reaction shows that protection of the alcohol is faster than the esterification reaction. Thus, it is convenient to monitor the reaction and extent the reaction time long enough to confirm the virtually quantitative formation of the ester (less than 0.5% of unreacted acid) in order to minimise the presence of bimatoprost free acid in the final product as an impurity.

Amidation of compound of formula (III) to obtain compound of formula (II) is carried out by reaction with EtNH$_2$, particularly with an aqueous solution of EtNH$_2$, in the presence or absence of an organic solvent. Thus, in a particular embodiment of the process of the invention, the solvent in step a) is selected from water and a mixture of water with an organic solvent. [not in claims] In another particular embodiment, optionally in combination with one or more features of the particular embodiments defined above, temperature of the amidation reaction is from 0 to 100° C., particularly from 20 to 40° C., more particularly from 25° C. to 33° C. Thus, as an instance, the amidation reaction can be performed in a 70% aqueous solution of ethylamine (EtNH$_2$) and at a temperature from 20 to 40° C., particularly from 25° C. to 33° C. Different amounts of the aqueous solution of EtNH$_2$ can be added depending on the solvent used. Generally, 10 ml of 70% aqueous solution of per gram of prostaglandin can be added.

Depending on the protecting group used, the amidation reaction time at 20° C. can be from 15-72 hours. By increasing the reaction temperature the reaction rate is increased but also the presence of bimatoprost free acid in the final product. Nevertheless, even so, levels of this impurity are significantly reduced compare with the processes of the prior art, as can be shown in Example 4.

Finally, bimatoprost is obtained from compound of formula (II) by deprotection of the hydroxyl groups in acidic medium. Any strong inorganic or organic acid can be used. The reaction can be carried out in any suitable solvent, particularly in a water-miscible solvent such as C$_1$-C$_4$ alcohols such as ethanol and isopropanol, acetonitrile, tetrahydrofurane, dimethyl sulfoxide, and dimethylformamide.

Thus, in a particular embodiment of the process of the invention, optionally in combination with one or more features of the particular embodiments defined above, deprotection is made in the presence of a strong inorganic or organic acid such as HCl or CF$_3$COOH. Particularly, deprotection is made in the presence of HCl. More particularly, the acid is either in stoichiometric or in catalytic amounts.

Advantageously, in the process of the invention reaction times of the deprotection reaction are significantly reduced compared to the processes of the prior art. Depending on the protecting group, the deprotection reaction can take up to 12 hours when performed at 20-25° C. Nevertheless, the reaction rate can be significantly increased by increasing the reaction temperature. As an instance, the deprotection reaction of compound of formula (II) wherein R$^1$ is butyl and R$^2$ is H (i.e. the protection was carried out with butyl vinyl ether) performed in the presence of hydrochloric acid at pH 0.5-1.5 and at 20° C. takes about 12 hours, while at 40° C. is completed in less than 2 hours, and at 50° C. is completed in 1 hour (see Example 4c below).

As mentioned above, compounds of formula (III)

(III)

wherein R$^1$ and R$^2$ are as defined above, and of formula (II)

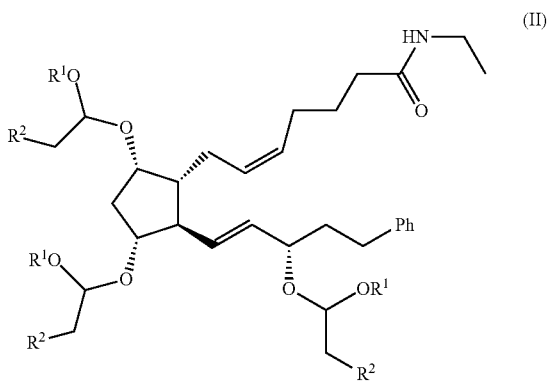

(II)

wherein R$^1$ and R$^2$ are as defined above or, alternatively, R$^1$ and R$^2$ taken together are selected from the group consisting of —CH$_2$—CH$_2$—, —O—CH$_2$—CH$_2$—, and —O—CH═CH—, which are intermediates useful for the preparation of bimatoprost, also form part of the invention.

In a particular embodiment, in compounds of formula (III) and (II) R$^1$ is a (C$_1$-C$_4$)alkyl and R$^2$ is H. More particularly, R$^1$ is selected from ethyl and n-butyl and R$^2$ is H.

In a more particular embodiment, in compounds of formula (III) R$^1$ and R$^2$ taken together are selected from the group consisting of —CH$_2$—CH$_2$—CH$_2$—, —CH$_2$—CH$_2$—, —O—CH$_2$—CH$_2$—, and —O—CH═CH—. More particularly, R$^1$ and R$^2$ taken together are —CH$_2$—CH$_2$—CH$_2$—.

In a more particular embodiment, in compounds of formula (II) R$^1$ and R$^2$ taken together are selected from the group consisting of —CH$_2$—CH$_2$—, —O—CH$_2$—CH$_2$—, and —O—CH═CH—.

The intermediate compounds mentioned herein above can be used for the following steps without further purification or can be effectively separated and purified by employing a conventional method well known to those skilled in the art, such as recrystallization, column chromatography, or by transformation into a salt or by washing with an organic solvent or with an aqueous solution, eventually adjusting the pH. In any case, in each reaction stage any one of the solvents mentioned above can be used. In a particular embodiment, the process for the preparation of bimatoprost is carried out from compound of formula (VIII) without the isolation of the different intermediates.

With the process of the invention bimatoprost crude is obtained with high purity and very good yields. Particularly, bimatoprost with a purity higher to 97.0% is obtained. The main byproducts are the trans isomer of compound of formula (V)

Trans-(V)

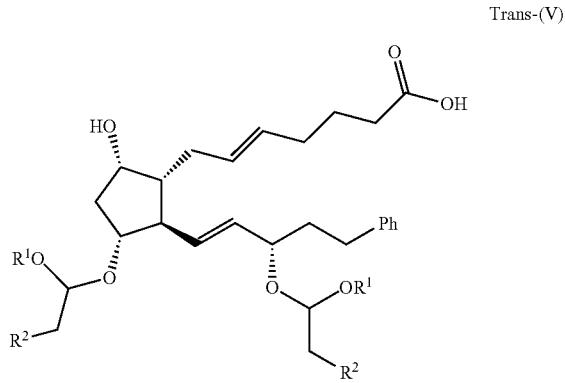

generated in the Wittig reaction in an amount of about 2.0%, and small amounts of the epimer (S) of compound of formula (V) in the C3 or the ω chain Eipmer (S)-(V)

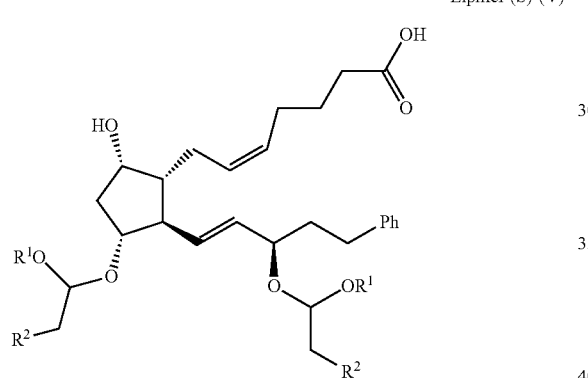

in an amount of less than 0.5% (the epimer (S) of compound of formula (VIII) is already present in the commercialized compound in amounts usually below 0.3%).

Additionally, overall yield from compound of formula (V) to crude bimatoprost range from 85.0 to 91.0%, depending on the specific protecting group.

Bimatoprost with a purity of at least 99.5% can be obtained by submitting this crude to conventional purification techniques or other techniques described in the prior art such as crystallization, chromatography, or a combination thereof.

Thus, taking into account all the advantages above mentioned, the alternative process to obtain bimatoprost of the present invention can be clearly considered more efficient and advantageous than those previously disclosed in the art.

Throughout the description and claims the word "comprise" and variations of the word, are not intended to exclude other technical features, additives, components, or steps. Furthermore, the word "comprise" encompasses the case of "consisting of". The following examples are provided by way of illustration, and they are not intended to be limiting of the present invention. Furthermore, the present invention covers all possible combinations of particular and preferred embodiments described herein.

EXAMPLES

Example 1. Preparation of (Z)-7-((1R,2R,3R,5S)-3-(1-butoxyethoxy)-2-((3S,E)-3-(1-butoxyethoxy)-5-phenylpent-1-en-1-yl)-5-hydroxycyclopentyl)hept-5-enoic Acid

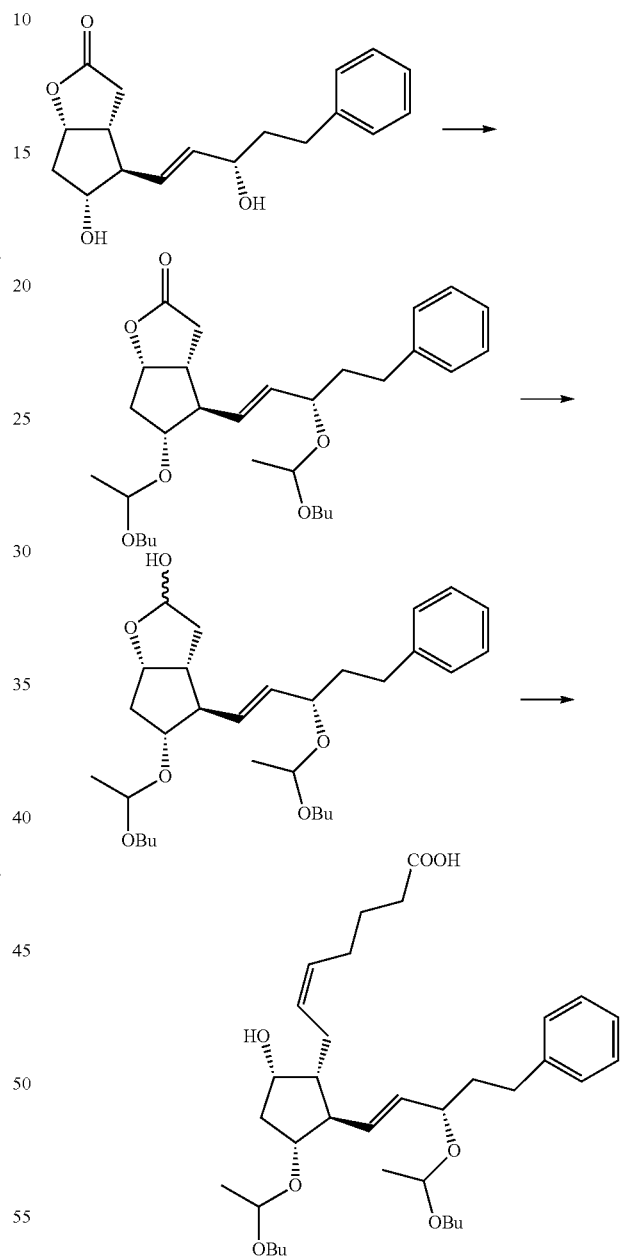

Example 1a. Preparation of (3aR,4R,5R,6aS)-5-(1-butoxyethoxy)-4-((3S,E)-3-(1-butoxyethoxy)-5-phenylpent-1-en-1-yl)hexahydro-2H-cyclopenta[b]furan-2-one In a three-necked flask under nitrogen atmosphere (3aR, 4R,5R,6aS)-5-hydroxy-4-((S,E)-3-hydroxy-5-phenylpent-1-en-1-yl)hexahydro-2H-cyclopenta[b]furan-2-one (10.0 g, 33.1 mmol), butyl vinyl ether (36.44 g, 364.1 mmol), pyridinium p-toluensulfonate (0.42 g, 1.66 mmol), and 90 ml of toluene were added. The resulting suspension was stirred at 20-25° C. from 90 to 180 min until complete dissolution. Once the mixture was dissolved, the end of the reaction was monitored by thin-layer chromatography (TLC). Once the reaction was completed 100 ml of a saturated NaHCO$_3$ solution were added, the mixture was stirred, then allowed to stand, and the phases were separated. The resulting organic phase was washed with 50.0 ml of a NaCl saturated solution, and after stirring and allowing standing the solution the phases were separated. The final organic phase was dried over anhydrous Na$_2$SO$_4$, filtered and the resulting solution was concentrated at vacuum to completely remove the solvents. A pale yellow oil of (3aR, 4R,5R,6aS)-5-(1-butoxyethoxy)-4-((3S,E)-3-(1-butoxyethoxy)-5-phenylpent-1-en-1-yl)hexahydro-2H-cyclopenta[b]furan-2-one (16.63 g, 33.1 mmol) as as a mixture of diastereoisomers was obtained which was used in the next step without any purification.

Example 1b. Preparation of (3aR,4R,5R,6aS)-5-(1-butoxyethoxy)-4-((3S,E)-3-(1-butoxyethoxy)-5-phenylpent-1-en-1-yl)hexahydro-2H-cyclopenta[b]furan-2-ol The residue obtained in Example 1 (16.63 g, 33.1 mmol) was dissolved in 150 ml of anhydrous tetrahydrofuran (THF) under nitrogen atmosphere. The resulting yellow solution was cooled to from −5 to 0° C. and added drop wise a 25.0% w/w solution of diisobutylaluminium hydride (26.7 mL, 39.72 mmol) in toluene maintaining the temperature range. Once the addiction is finished the mixture was stirred at 0° C. for 60 min and the reaction was monitored by TLC. Once the reaction is completed the mixture was cooled down to −20° C. and 2.0 ml of methanol were added. The resulting slightly yellow solution was stirred at 0° C. for 15 minutes and then 150 ml of a saturated solution of potassium sodium tartrate tetrahydrate and 150 ml of ethyl acetate were added, and the mixture was stirred, allowed to settle and phases were separated. The resulting aqueous phase was stirred with 50 ml of ethyl acetate. The combined organic phases were washed with a saturated solution of NaCl and water successively. The final organic phase was dried over anhydrous Na$_2$SO$_4$, filtered and the resulting solution concentrated at vacuum to a residue. A reaction crude as a yellow oil containing the title compound as a mixture of diastereomers was obtained and was used in the next step without any further purification.

Example 1c. Preparation of (Z)-7-((1R,2R,3R,5S)-3-(1-butoxyethoxy)-2-((3S,E)-3-(1-butoxyethoxy)-5-phenylpent-1-en-1-yl)-5-hydroxycyclopentyl)hept-5-enoic Acid In a three-necked flask equipped with a thermometer and nitrogen gas inlet 4-(carboxybutyl)triphenylphosphonium bromide (36.68 g, 82.75 mmol) and 150.0 ml of anhydrous THF were added under inert atmosphere. The resulting suspension was cooled down to from −5 to 0° C. and potassium tert-butoxide (18.57 g, 165.5 mmol) was added portion wise maintaining the temperature range. The resulting orange suspension was stirred at −5-0° C. for 60 minutes. Then, (3aR,4R,5R,6aS)-5-(1-butoxyethoxy)-4-((3S,E)-3-(1-butoxyethoxy)-5-phenylpent-1-en-1-yl)hexahydro-2H-cyclopenta[b]furan-2-ol obtained in the example 2 as a crude reaction dissolved in 50.0 ml of anhydrous THF was added. The orange suspension was stirred at 0° C. for 3 hours and the end of the reaction was controlled by TLC. Once the reaction is completed, 100.0 ml of water and 100.0 ml of ethyl acetate were added and the pH was adjusted between 3.0 and 4.0 with a 1.0 N hydrochloric acid solution. The phases were separated and the resulting organic phase was washed twice with 50 ml of water. The resulting organic phase was dried over anhydrous Na$_2$SO$_4$, filtered and concentrated under vacuum. The obtained residue was purified by column chromatography (3.5×40 cm, 200 g silica) eluting with a 50:49:1 mixture of heptane:tert-butyl methyl ether (MTBE):AcOH. 18.30 g (94.0% yield) of a diastereomeric mixture of (Z)-7-((1R,2R,3R,5S)-3-(1-butoxyethoxy)-2-((3S,E)-3-(1-butoxyethoxy)-5-phenylpent-1-en-1-yl)-5-hydroxycyclopentyl)hept-5-enoic acid as a colourless oil were isolated.

$^1$H-NMR (CDCl$_3$, 400 MHz) δ (ppm): 7.30-7.23 (2H, m, CH), 7.20-7.14 (3H, m, CH), 5.57-5.32 (4H, m, H$\underline{C}$=C$\underline{H}$), 4.77-4.69 (2H, m, OC$\underline{H}$(CH$_3$)OBu), 4.17-4.11 (1H, m, CH), 4.10-3.91 (2H, m, CH), 3.66-3.32 (4H, m, OC $\underline{H}_2$CH$_2$CH$_2$CH$_3$), 2.76-2.59 (2H, m, C$\underline{H}_2$Ph), 2.49-2.38 (1H, m, CH), 2.36-2.23 (3H, m, CH$_2$), 2.21-1.74 (7H, m, CH$_2$), 1.72-1.63 (2H, m, CH$_2$), 1.56-1.45 (5H, m, CH+OCH$_2$C $\underline{H}_2$CH$_2$CH$_3$), 1.41-1.33 (4H, m, OCH$_2$CH$_2$C$\underline{H}_2$CH$_3$), 1.33-1.25 (6H, m, OCH(C$\underline{H}_3$)OBu), 0.94-0.87 (6H, m, OCH$_2$CH$_2$CH$_2$C$\underline{H}_3$).

MS (ESI+): [M+NH$_4$]$^+$ observed m/z=606.4347, calculated m/z=606.4364; [M+Na]$^+$ observed m/z=611.3907, calculated m/z=611.3918.

Example 2. (Z)-7-((1R,2R,3R,5S)-3-(1-ethoxyethoxy)-2-((3S,E)-3-(1-ethoxyethoxy)-5-phenylpent-1-en-1-yl)-5-hydroxycyclopentyl)hept-5-enoic Acid

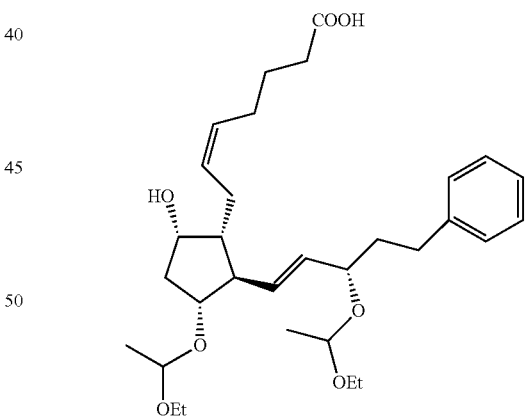

Using ethyl vinyl ether as protective agent, and operating analogously to Example 1, a crude containing (Z)-7-((1R, 2R,3R,5S)-3-(1-ethoxyethoxy)-2-((3S,E)-3-(1-ethoxyethoxy)-5-phenylpent-1-en-1-yl)-5-hydroxycyclopentyl) hept-5-enoic acid was obtained. This crude was purified by column chromatography (3.5×40 cm, 200 g silica) using a 50:49:1 mixture of heptane:MTBE:AcOH as eluent. 16.38 g (93.0% yield) of a diastereomeric mixture of ((Z)-7-((1R, 2R,3R,5S)-3-(1-ethoxyethoxy)-2-((3S,E)-3-(1-ethoxyethoxy)-5-phenylpent-1-en-1-yl)-5-hydroxycyclopentyl) hept-5-enoic acid were isolated as a colourless oil.

¹H-NMR (CDCl₃, 400 MHz) δ (ppm): 7.30-7.24 (2H, m, CH), 7.20-7.14 (3H, m, CH), 5.57-5.31 (4H, m, CH), 4.77-4.69 (2H, m, CH), 4.17-4.11 (1H, m, CH), 4.10-3.91 (2H, m, CH), 3.74-3.38 (4H, m, CH₂), 2.77-2.59 (2H, m, CH₂), 2.50-2.40 (1H, m, CH), 2.37-2.23 (3H, m, CH₂), 2.21-2.07 (7/2H, m, CH₂), 2.04-1.90 (3/2H, m, CH₂), 1.90-1.74 (2H, m, CH₂), 1.73-1.62 (2H, m, CH₂), 1.55-1.45 (1H, m, CH), 1.32-1.27 (6H, m, CH₃), 1.20-1.14 (6H, m, CH₃).

MS (ESI+): [M+NH₄]⁺ observed m/z=550.3729, calculated m/z=550.3738; [M+Na]⁺ observed m/z=555.3286, calculated m/z=555.3292.

Example 3. (Z)-7-((1R,2R,3R,5S)-5-hydroxy-2-((3S,E)-5-phenyl-3-((tetrahydro-2H-pyran-2-yl)oxy)pent-1-en-1-yl)-3-((tetrahydro-2H-pyran-2-yl)oxy)cyclopentyl)hept-5-enoic Acid

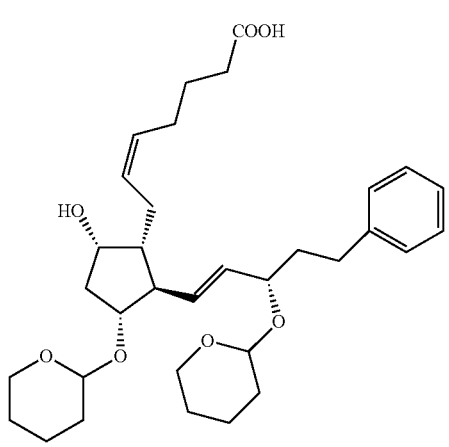 [SMILES: O=C(O)CCC/C=C\C[C@@H]1[C@@H](/C=C/[C@H](CCc2ccccc2)OC2CCCCO2)[C@H](OC2CCCCO2)C[C@@H]1O]

Using 3,4-dihydro-2H-pyran as protective agent, and operating analogously to Example 1, a crude containing (Z)-7-((1R,2R,3R,5S)-5-hydroxy-2-((3S,E)-5-phenyl-3-((tetrahydro-2H-pyran-2-yl)oxy)pent-1-en-1-yl)-3-((tetrahydro-2H-pyran-2-yl)oxy)cyclopentyl) hept-5-enoic acid was obtained. This crude was purified by column chromatography (3.5×40 cm, 200 g silica) using a 50:49:1 mixture of heptane:MTBE:AcOH as eluent. 17.31 g (94.0% yield) of a diastereomeric mixture of (Z)-7-((1R,2R,3R,5S)-5-hydroxy-2-((3S,E)-5-phenyl-3-((tetrahydro-2H-pyran-2-yl)oxy)pent-1-en-1-yl)-3-((tetrahydro-2H-pyran-2-yl)oxy)cyclopentyl)hept-5-enoic acid were isolated.

¹H-NMR (CDCl₃, 400 MHz) δ (ppm): 7.29-7.23 (2H, m, CH), 7.21-7.14 (3H, m, CH), 5.65-5.31 (4H, m, CH), 4.77-4.65 (2H, m, CH), 4.18-4.03 (3H, m, CH), 3.95-3.78 (2H, m, CH₂), 3.55-3.42 (2H, m, CH₂), 2.77-2.59 (2H, m, CH₂), 2.57-2.38 (1H, m, CH), 2.26-2.07 (6H, m, CH₂), 2.05-1.75 (6H, m, CH₂), 1.75-1.61 (4H, m, CH₂), 1.61-1.44 (8H, m, CH₃), 1.58-1.45 (1H, m, CH).

MS (ESI+): [M+NH₄]⁺ observed m/z=574.3746, calculated m/z=574.3738; [M+Na]⁺ observed m/z=579.3297, calculated m/z=579.3292.

Example 4. Preparation of Bimatoprost from Compound of Formula (III) Wherein R¹ is Butyl and R² is H

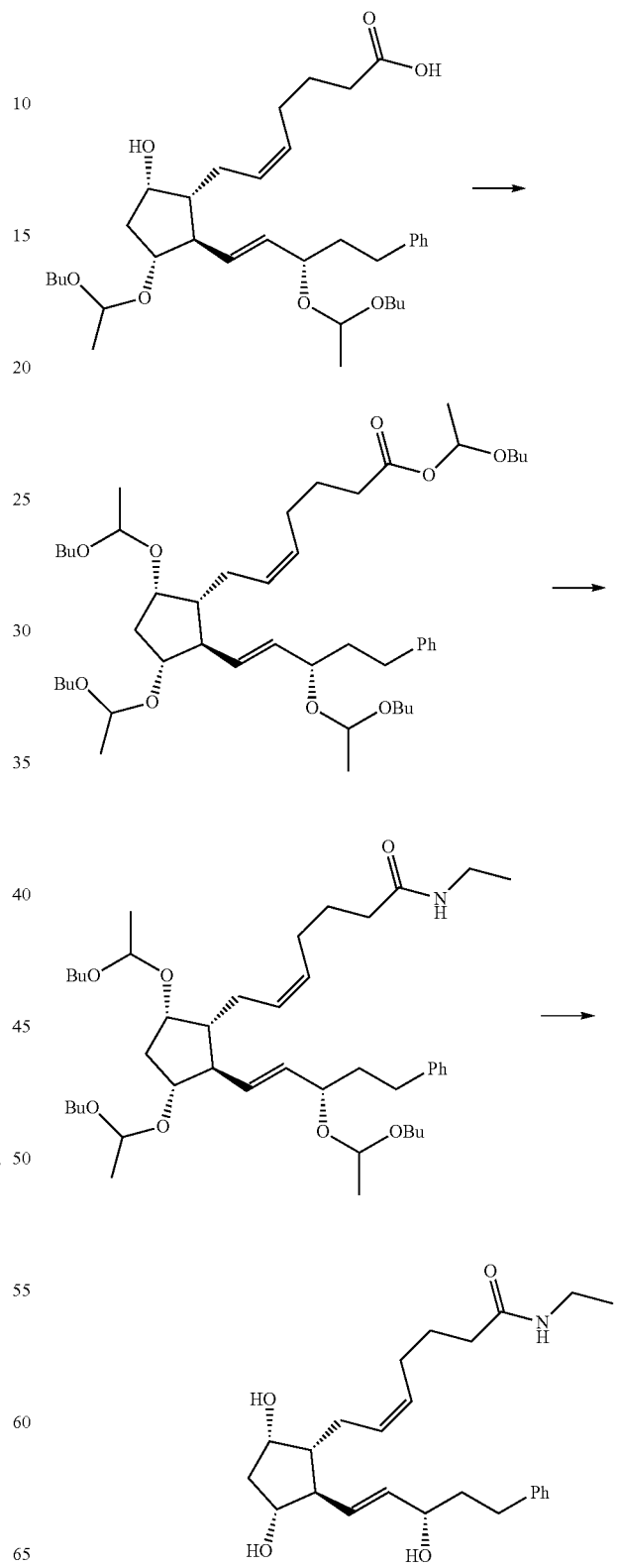

Example 4a. (Z)-1-butoxyethyl 7-((1R,2R,3R,5S)-3,5-bis(1-butoxyethoxy)-2-((3S,E)-3-(1-butoxy-ethoxy)-5-phenylpent-1-en-1-yl)cyclopentyl)hept-5-enoate 44.3 ml of Butyl vinyl ether (0.3418 mol) were added to a mixture of 18.30 g (0.0310 mol) of (Z)-7-((1R,2R,3R,5S)-3-(1-butoxyethoxy)-2-((3S,E)-3-(1-butoxyethoxy)-5-phenylpent-1-en-1-yl)-5-hydroxycyclopentyl)hept-5-enoic acid and 1.56 g (0.0062 mol) of pyridinium p-toluenesulfonate (PPTS) in 50 ml of toluene. After stirring for 3 h at 25° C. the completion of the reaction was checked by TLC. The resulting reaction mixture was then diluted in 50 ml of toluene and washed with 50 ml of an aqueous solution of NaHCO$_3$ (7%). After separation of the layers, the organic layer was washed with 50 ml of demineralized water. Then, the layers were separated again and the organic layer was concentrated and dried at vacuum. The diastereomeric mixture of (Z)-1-butoxyethyl 7-((1R,2R,3R,5S)-3,5-bis(1-butoxyethoxy)-2-((3S,E)-3-(1-butoxyethoxy)-5-phenyl pent-1-en-1-yl)cyclo pentyl)hept-5-enoate was obtained in a quantitative yield (24.53 g) as a yellowish oil which was used in the next step without further purification. Alternatively, this oil can be purified by flash chromatography on silica using as eluent a 97:2:1 mixture of heptane:EtOAc:Et$_3$N to obtain the corresponding pure diastereomeric mixture.

R$_f$ on a silica TLC (Heptane:EtOAc 1:1): 0.60
$^1$H-NMR (CDCl$_3$, 400 MHz) δ (ppm): 0.95-0.86 (12H, m, OCH$_2$CH$_2$CH$_2$CH$_3$), 1.30-1.23 (9H, m, OCH(CH$_3$)OBu), 1.42-1.30 (11H, m, COOCH(CH$_3$)OBu+OCH$_2$CH$_2$CH$_2$CH$_3$), 1.58-1.46 (1H, m, CH), 1.59-1.45 ((8H, m, OCH$_2$CH$_2$CH$_2$CH$_3$), 1.70-1.61 (2H, m, CH$_2$), 2.35-1.72 (10H, m, CH$_2$), 2.55-2.43 (1H, m, CH), 2.77-2.60 (2H, m, CH$_2$Ph), 3.76-3.36 (8H, m, OCH$_2$CH$_2$CH$_2$CH$_3$), 4.15-3.77 (3H, m, PGOCH), 4.77-4.61 (3H, m, ROCH(CH$_3$)OBu), 5.61-5.28 (4H, m, CH=CH), 5.92-5.88 (1H, m, COOCH(CH$_3$)OBu), 7.20-7.14 (3H, m, Ar—H), 7.27-7.23 (2H, m, Ar—H).
MS (ESI+): [M+NH$_4$]$^+$ observed m/z=806.6181, calculated m/z=806.6141; [M+Na]$^+$ observed m/z=811.5732, calculated m/z=811.5695.

Example 4b. (Z)-7-((1R,2R,3R,5S)-3,5-bis(1-butoxyethoxy)-2-((3S,E)-3-(1-butoxyethoxy)-5-phenyl-pent-1-en-1-yl)cyclopentyl)-N-ethylhept-5-enamide 94 ml of a 70% solution of ethylamine in water (1.182 mol) were added over 24.53 g of the last reaction crude, the yellowish oil which consists in (Z)-1-butoxyethyl 7-((1R,2R,3R,5S)-3,5-bis(1-butoxyethoxy)-2-((3S,E)-3-(1-butoxy-ethoxy)-5-phenylpent-1-en-1-yl)cyclopentyl) hept-5-enoate. The resulting mixture was stirred at 20° C. for 72 h. The completion of the reaction was checked by TLC. After the reaction was completed, 94 ml of toluene were added and the resulting mixture was washed with 47 ml of a 5% aqueous solution of NaCl. After separation of the layers, the top organic layer was washed with 47 ml of demineralized water. Then, the layers were separated again and the organic one was concentrated and dried at vacuum to obtain 23.20 g of a yellowish oil which essentially consists on a diastereomeric mixture of (Z)-7-((1R,2R,3R,5S)-3,5-bis(1-butoxyethoxy)-2-((3S,E)-3-(1-butoxyethoxy)-5-phenylpent-1-en-1-yl)cyclo pentyl)-N-ethylhept-5-enamide. It was used in the next step without further purification. Alternatively, this oil can be purified by flash chromatography on silica using as eluent a 80:19:1 mixture of heptane:EtOAc:Et$_3$N to obtain the corresponding pure diastereomeric mixture.

R$_f$ on a silica TLC (Heptane:EtOAc 1:1): 0.30
$^1$H-NMR (CDCl$_3$, 400 MHz) δ (ppm): 0.94-0.87 (9H, m, OCH$_2$CH$_2$CH$_2$CH$_3$), 1.12-1.06 (3H, m, NHCH$_2$CH$_3$), 1.30-1.23 (9H, m, OCH(CH$_3$)OEt), 1.42-1.30 (6H, m, OCH$_2$CH$_2$CH$_2$CH$_3$), 1.56-1.46 (7H, m, CH+OCH$_2$CH$_2$CH$_2$CH$_3$), 1.57-1.46 (1H, m, CH), 1.70-1.58 (2H, m, CH$_2$), 2.34-1.73 (10H, m, CH$_2$), 2.55-2.43 (1H, m, CH), 2.76-2.60 (2H, m, CH$_2$Ph), 3.27-3.18 (2H, m, NHCH$_2$CH$_3$), 3.68-3.29 (6H, m, OCH$_2$CH$_2$CH$_2$CH$_3$), 4.17-3.78 (3H, m, PGOCH), 4.76-4.60 (3H, m, ROCH(CH$_3$)OBu), 5.60-5.28 (5H, m, NH+CH=CH), 7.20-7.15 (3H, m, Ar—H), 7.29-7.25 (2H, m, Ar—H).
MS (ESI+): [M+NH$_4$]$^+$ observed m/z=733.5770, calculated m/z=733.5725; [M+Na]$^+$ observed m/z=738.5327, calculated m/z=738.5279.

Example 4c. Bimatoprost 94 ml of THF and 19 ml of demineralized water were added to the 24.53 g of the last reaction crude, the yellowish oil which consists on (Z)-7-((1R,2R,3R,5S)-3,5-bis(1-butoxyethoxy)-2-((3S,E)-3-(1-butoxyethoxy)-5-phenylpent-1-en-1-yl)cyclo pentyl)-N-ethylhept-5-enamide. It was stirred and then, the pH value of the mixture was adjusted pH=1.0 with 37% aqueous HCl. The resulting reaction mixture was stirred for 1 h at 50° C. The completion of the reaction was checked by TLC. After the reaction was completed, 19 ml of demineralized water were added to the mixture and THF was removed by vacuum suction. The mixture was extracted twice with 47 ml of EtOAc and the both organic layers were combined and washed with 47 ml of demineralized water. Then, the layers were separated again and the organic one was concentrated at vacuum. In order to dry it properly, the residual oil was twice solved in 30 ml of EtOAc and concentrated at vacuum. The resulting crude, 12.25 g of a yellowish solid, contained Bimatoprost as main product. The crude was purified by flash chromatography on silica using a 8:2 heptane/acetone mixture as eluent affording 11.30 g (87.5% overall yield) of pure bimatoprost as a white solid.

R$_f$ on a silica TLC (MTBE:EtOH 9:1): 0.35
HRMS (ESI+): [M+Na]$^+$ observed m/z=438.2614, calculated m/z=438.2615; [2M+Na]$^+$ observed m/z=853.5317, calculated m/z=853.5337.

Example 5. Preparation of Bimatoprost from Compound of Formula (III) Wherein R$^1$ is Ethyl and R$^2$ is H

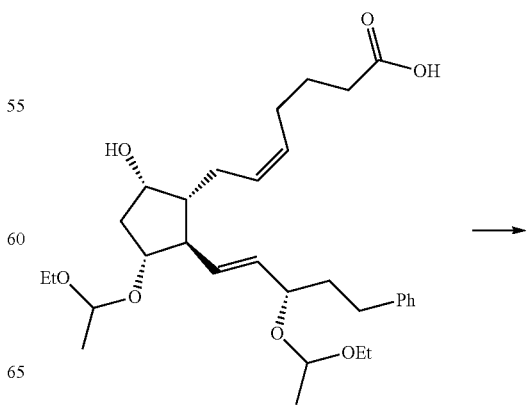

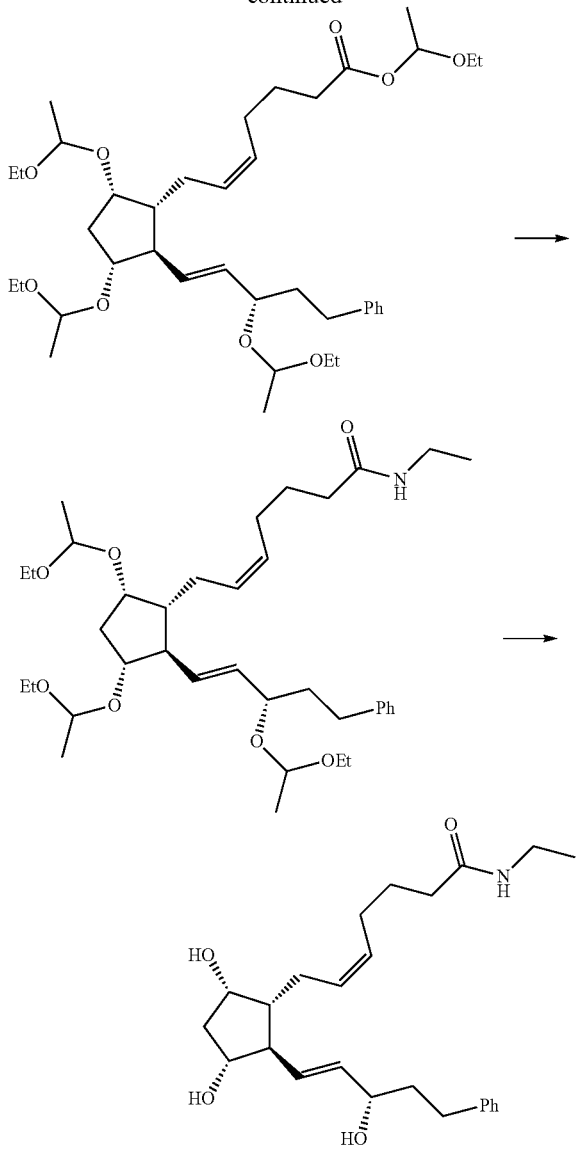

Example 5a. (Z)-1-ethoxyethyl 7-((1R,2R,3R,5S)-3,5-bis(1-ethoxyethoxy)-2-((3S,E)-3-(1-ethoxyethoxy)-5-phenylpent-1-en-1-yl)cyclopentyl)hept-5-enoate 11.0 ml of Ethyl vinyl ether (0.1144 mol) were added to a mixture of 5.53 g (0.0104 mol) of (Z)-7-((1R,2R,3R,5S)-3-(1-ethoxyethoxy)-2-((3S,E)-3-(1-ethoxyethoxy)-5-phenylpent-1-en-1-yl)-5-hydroxycyclopentyl)hept-5-enoic acid and 0.52 g (0.00208 mol) of PPTS in 16 ml of toluene. After stirring for 3 h at 25° C. the completion of the reaction was checked by TLC. The resulting reaction mixture was then diluted in 16 ml of toluene and washed with 16 ml of an aqueous solution of NaHCO$_3$ (7%). After separation of the layers, the organic layer was washed with 16 ml of demineralized water. Then, the layers were separated again and the organic layer was concentrated and dried at vacuum. The diastereomeric mixture of (Z)-1-ethoxyethyl 7-((1R,2R,3R,5S)-3,5-bis(1-ethoxyethoxy)-2-((3S,E)-3-(1-ethoxyethoxy)-5-phenylpent-1-en-1-yl)cyclopentyl)hept-5-enoate was obtained in a quantitative yield (7.05 g) as a yellowish oil which was used in the next step without further purification. Alternatively, this oil can be purified by flash chromatography on silica using as eluent a 97:2:1 mixture of heptane:EtOAc:Et$_3$N to obtain the corresponding pure diastereomeric mixture.

R$_f$ on a silica TLC (Heptane:EtOAc 1:1): 0.70

$^1$H-NMR (CDCl$_3$, 400 MHz) δ (ppm): 1.23-1.12 (12H, m, OCH$_2$C$\underline{H}_3$), 1.31-1.24 (9H, m, OCH(C$\underline{H}_3$)OEt), 1.38 (3H, d, J=5.4, COOCH(C$\underline{H}_3$)OEt), 1.57-1.43 (1H, m, CH), 1.70-1.61 (2H, p, J=7.1, CH$_2$), 2.35-1.72 (10H, m, CH$_2$), 2.55-2.43 (1H, m, CH), 2.77-2.60 (2H, m, C$\underline{H}_2$Ph), 3.76-3.36 (8H, m, OC$\underline{H}_2$CH$_3$), 4.15-3.78 (3H, m, PGOC$\underline{H}$), 4.77-4.61 (3H, m, ROC$\underline{H}$(CH$_3$)OEt), 5.69-5.28 (4H, m, C$\underline{H}$=C$\underline{H}$), 5.95-5.89 (1H, m, COOC$\underline{H}$(CH$_3$)OEt), 7.21-7.13 (3H, m, Ar—$\underline{H}$), 7.30-7.23 (2H, m, Ar—$\underline{H}$).

MS (ESI+): [M+NH$_4$]$^+$ observed m/z=694.4871, calculated m/z=694.4889; [M+Na]$^+$ observed m/z=699.4424, calculated m/z=699.4443.

Example 5b. (Z)-7-((1R,2R,3R,5S)-3,5-bis(1-ethoxyethoxy)-2-((3S,E)-3-(1-ethoxyethoxy)-5-phenylpent-1-en-1-yl)cyclopentyl)-N-ethylhept-5-enamide 32 ml (0.402 mol) of a 70% solution of ethylamine in water were added over 7.05 g of the last reaction crude, the yellowish oil which consists in (Z)-1-ethoxyethyl 7-((1R,2R,3R,5S)-3,5-bis(1-ethoxyethoxy)-2-((3S,E)-3-(1-ethoxyethoxy)-5-phenylpent-1-en-1-yl)cyclopentyl) hept-5-enoate. The resulting mixture was stirred at 20° C. for 24 h. The completion of the reaction was checked by TLC. After the reaction was completed, 32 ml of toluene were added and the resulting mixture was washed with 16 ml of a 5% aqueous solution of NaCl. After separation of the layers, the top organic layer was washed with 16 ml of demineralized water. Then, the layers were separated again and the organic one was concentrated and dried at vacuum to obtain 6.24 g of a yellowish oil which essentially consists on a diastereomeric mixture of (Z)-7-((1R,2R,3R,5S)-3,5-bis(1-ethoxyethoxy)-2-((3S,E)-3-(1-ethoxyethoxy)-5-phenylpent-1-en-1-yl)cyclopentyl)-N-ethylhept-5-enamide. It was used in the next step without further purification. Alternatively, this oil can be purified by flash chromatography on silica using as eluent a 80:19:1 mixture of heptane:EtOAc:Et$_3$N to obtain the corresponding pure diastereomeric mixture.

R$_f$ on a silica TLC (Heptane:EtOAc 1:1): 0.35

$^1$H-NMR (CDCl$_3$, 400 MHz) δ (ppm): 1.13-1.06 (3H, m, NHCH$_2$C$\underline{H}_3$), 1.23-1.13 (9H, m, OCH$_2$C$\underline{H}_3$), 1.32-1.23 (9H, m, OCH(C$\underline{H}_3$)OEt), 1.57-1.46 (1H, m, CH), 1.70-1.58 (2H, m, CH$_2$), 2.40-1.73 (10H, m, CH$_2$), 2.55-2.42 (1H, m, CH), 2.77-2.60 (2H, m, C$\underline{H}_2$Ph), 3.28-3.18 (2H, m, NHC$\underline{H}_2$CH$_3$) 3.75-3.35 (6H, m, OC$\underline{H}_2$CH$_3$), 4.16-3.78 (3H, m, PGOC$\underline{H}$), 4.77-4.61 (3H, m, ROC$\underline{H}$(CH$_3$)OEt), 5.70-5.29 (5H, m, N H+C$\underline{H}$=C$\underline{H}$), 7.22-7.14 (3H, m, Ar—$\underline{H}$), 7.30-7.23 (2H, m, Ar—$\underline{H}$).

MS (ESI+): [M+NH$_4$]$^+$ observed m/z=649.4777, calculated m/z=649.4786; [M+Na]$^+$ observed m/z=654.4334, calculated m/z=654.4340.

Example 5c. Bimatoprost 32 ml of THF and 6.5 ml of demineralized water were added to the 6.24 g of the last reaction crude, the yellowish oil which consists on (Z)-7-((1R,2R,3R,5S)-3,5-bis(1-ethoxyethoxy)-2-((3S,E)-3-(1-ethoxyethoxy)-5-phenylpent-1-en-1-yl)cyclo pentyl)-N-ethylhept-5-enamide. It was stirred and then, the pH value of the mixture was adjusted pH=1.0 with 37% aqueous HCl. The resulting reaction mixture was stirred for 1 h at 50° C. The completion of the reaction was checked by TLC. After the reaction was completed, 7 ml of demineralized water were added to the mixture and THF was removed by vacuum suction. The mixture was extracted twice with 16 ml of EtOAc and the both organic layers were combined and washed with 16 ml of demineralized water. Then, the layers were separated again and the organic one was concentrated at vacuum. In order to dry it properly, the residual oil was twice solved in 10 ml of EtOAc and concentrated at vacuum. The resulting crude, 4.02 g of a yellowish solid, contained Bimatoprost as main product. The crude was purified by flash chromatography on silica using a 8:2 Heptane/Acetone mixture as eluent affording 3.89 g (90.0% overall yield) of pure Bimatoprost as a white solid.

Example 6. Preparation of Bimatoprost from Compound of Formula (III) Wherein $R^1$ and $R^2$ Together are —$CH_2$—$CH_2$—$CH_2$—

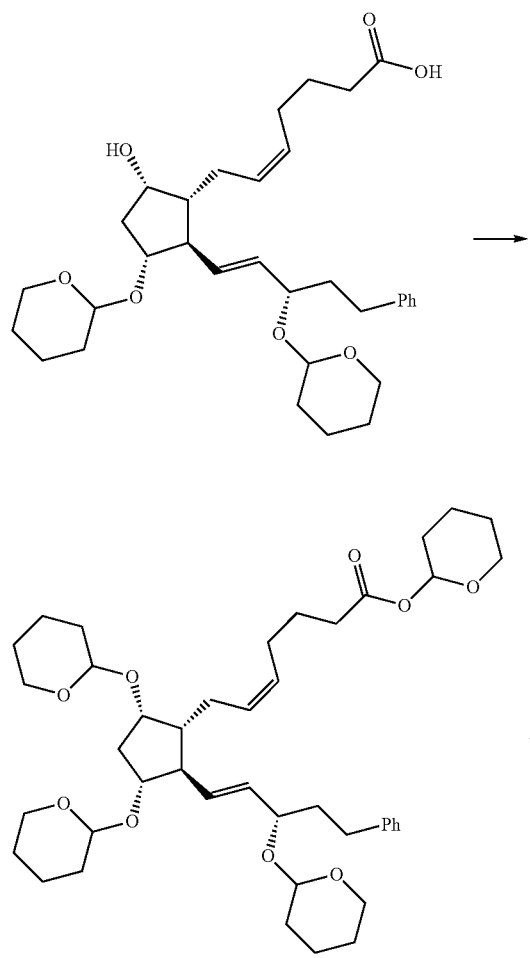

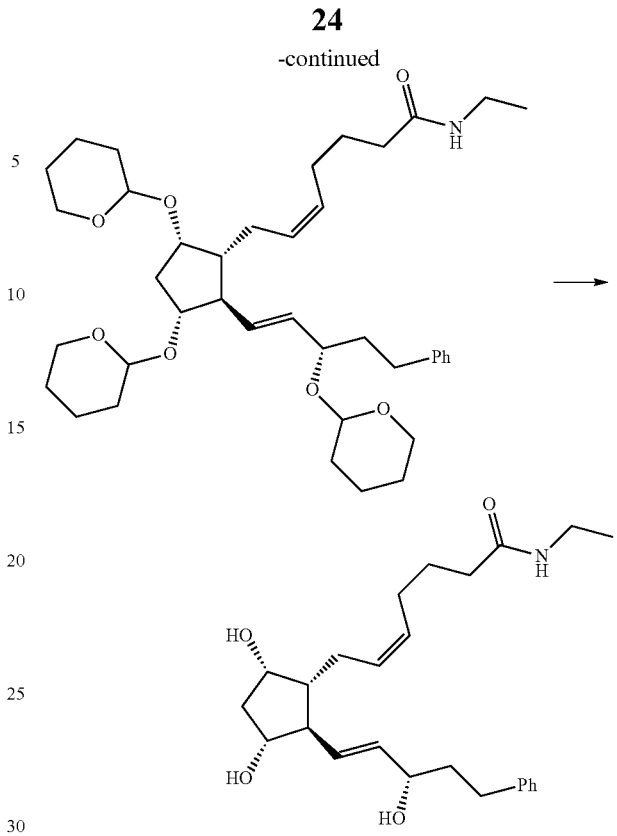

Example 6a. (Z)-tetrahydro-2H-pyran-2-yl 7-((1R, 2R,3R,5S)-2-((3S,E)-5-phenyl-3-((tetra hydro-2H-pyran-2-yl)oxy)pent-1-en-1-yl)-3,5-bis((tetrahydro-2H-pyran-2-yl)oxy)cyclopentyl)hept-5-enoate 14.3 ml of 3,4-dihydro-2H-pyran (0.157 mol) were added to a mixture of 7.94 g (0.01426 mol) of (Z)-7-((1R,2R,3R, 5S)-5-hydroxy-2-((3S,E)-5-phenyl-3-((tetra hydro-2H-pyran-2-yl)oxy)pent-1-en-1-yl)-3-((tetrahydro-2H-pyran-2-yl)oxy)cyclo pentyl)hept-5-enoic acid and 0.72 g (0.00285 mol) of PPTS in 20 ml of toluene. After stirring for 3 h at 25° C. the completion of the reaction was checked by TLC. The resulting reaction mixture was then diluted in 20 ml of toluene and washed with 20 ml of an aqueous solution of $NaHCO_3$ (7%). After separation of the layers, the organic layer was washed with 20 ml of demineralized water. Then, the layers were separated again and the organic layer was concentrated and dried at vacuum. The diastereomeric mixture of (Z)-tetrahydro-2H-pyran-2-yl 7-((1R,2R,3R,5S)-2-((3S,E)-5-phenyl-3-((tetrahydro-2H-pyran-2-yl)oxy)pent-1-en-1-yl)-3,5-bis((tetra hydro-2H-pyran-2-yl)oxy) cyclopentyl)hept-5-enoate was obtained in a quantitative yield (10.36 g) as a yellowish oil which was used in the next step without further purification. Alternatively, this oil can be purified by flash chromatography on silica using as eluent a 97:2:1 mixture of heptane:EtOAc:$Et_3N$ to obtain the corresponding pure diastereomeric mixture.

$R_f$ on a silica TLC (Heptane:EtOAc 1:1): 0.55

$^1$H-NMR (CDCl$_3$, 400 MHz) δ (ppm): 1.61-1.49 (1H, m, CH), 2.42-1.38 (36H, m, $CH_2$), 2.61-2.41 (1H, m, CH), 2.82-2.60 (2H, m, C$\underline{H}_2$Ph), 3.51-3.39 (3H, m, O—C $\underline{H}_2CH_2CH_2CH_2CH$—$O_2$), 3.70-3.63 (1H, m, O—C $\underline{H}_2CH_2CH_2CH_2CH$—$O_2$), 4.22-3.78 (7H, m, C $\underline{H}$-OTHP+O—C$\underline{H}_2CH_2CH_2CH_2CH$—$O_2$), 4.77-4.57 (3H, m, O—CH—O), 5.73-5.29 (4H, m, C<u>H</u>=C<u>H</u>), 5.95 (1H, s, COOC<u>H</u>—O), 7.21-7.14 (3H, m, Ar—<u>H</u>), 7.29-7.24 (2H, m, Ar—<u>H</u>).

MS (ESI+): [M+NH$_4$]$^+$ observed m/z=742.4861, calculated m/z=742.4889; [M+Na]$^+$ observed m/z=747.4414, calculated m/z=747.4443.

Example 6b. (Z)—N-ethyl-7-((1R,2R,3R,5S)-2-((3S,E)-5-phenyl-3-((tetrahydro-2H-pyran-2-yl)oxy)pent-1-en-1-yl)-3,5-bis((tetrahydro-2H-pyran-2-yl)oxy)cyclopentyl) hept-5-enamide 43 ml (0.541 mol) of a 70% solution of ethylamine in water were added over 10.36 g of the last reaction crude, the yellowish oil which consists in (Z)-tetrahydro-2H-pyran-2-yl 7-((1R,2R,3R,5S)-2-((3S,E)-5-phenyl-3-((tetrahydro-2H-pyran-2-yl) oxy)pent-1-en-1-yl)-3,5-bis((tetrahydro-2H-pyran-2-yl)oxy)cyclopentyl)hept-5-enoate. The mixture was stirred at 20° C. for 20 h. The completion of the reaction was checked by TLC. After the reaction was completed, 43 ml of toluene were added and the resulting mixture was washed with 22 ml of a 5% aqueous solution of NaCl. After separation of the layers, the top organic layer was washed with 22 ml of demineralized water adjusting pH=6 with 37% aqueous HCl. Then, the layers were separated again and the organic one was concentrated and dried at vacuum to obtain 10.08 g of a yellowish oil which essentially consists on a diastereomeric mixture of (Z)—N-ethyl-7-((1R,2R,3R,5S)-2-((3S,E)-5-phenyl-3-((tetrahydro-2H-pyran-2-yl) oxy)pent-1-en-1-yl)-3,5-bis((tetrahydro-2H-pyran-2-yl)oxy)cyclopentyl)hept-5-enamide. It was used in the next step without further purification. Alternatively, this oil can be purified by flash chromatography on silica using as eluent a 80:19:1 mixture of heptane:EtOAc:Et$_3$N to obtain the corresponding pure diastereomeric mixture.

R$_f$ on a silica TLC (Heptane:EtOAc 1:1): 0.25

$^1$H-NMR (CDCl$_3$, 400 MHz) δ (ppm): 1.12-1.06 (3H, m, NHCH$_2$C<u>H</u>$_3$), 1.62-1.49 (1H, m, CH), 2.40-1.39 (30H, m, CH$_2$), 2.62-2.41 (1H, m, CH), 2.82-2.61 (2H, m, C<u>H</u>$_2$Ph), 3.37-3.17 (2H, m, NHC<u>H</u>$_2$CH$_3$) 3.52-3.40 (3H, m, O—C <u>H</u>$_2$CH$_2$CH$_2$CH$_2$CH—O$_2$), 4.22-3.79 (6H, m, C <u>H</u>—OTHP+O—C<u>H</u>$_2$CH$_2$CH$_2$CH$_2$CH—O$_2$), 4.78-4.56 (3H, m, CH), 5.71-5.29 (5H, m, N<u>H</u>+C<u>H</u>=C<u>H</u>), 7.23-7.14 (3H, m, Ar—<u>H</u>), 7.30-7.24 (2H, m, Ar—<u>H</u>).

MS (ESI+): [M+NH$_4$]$^+$ observed m/z=685.4785, calculated m/z=685.4786; [M+Na]$^+$ observed m/z=690.4342, calculated m/z=690.4340.

Example 6c. Bimatoprost, (Z)-7-((1R,2R,3R,5S)-3, 5-dihydroxy-2-((S,E)-3-hydroxy-5-phenylpent-1-en-1-yl)cyclopentyl)-N-ethylhept-5-enamide 43 ml of MeOH and 1.08 g of PPTS were added to the last obtained yellowish oil, which essentially consists on a diastereomeric mixture of (Z)—N-ethyl-7-((1R,2R,3R,5S)-2-((3S,E)-5-phenyl-3-((tetrahydro-2H-pyran-2-yl)oxy)pent-1-en-1-yl)-3,5-bis((tetrahydro-2H-pyran-2-yl)oxy)cyclopentyl) hept-5-enamide. The resulting mixture was stirred at 25° C. for 24 h. The completion of the reaction was checked by TLC. After the reaction was completed, 22 ml of demineralized water were added and the pH value of the mixture was adjusted pH=7.0 with KOH 20%. Then, MeOH was removed by vacuum suction, in order to do it properly, the residual aqueous phase was twice mixed with 10 ml of EtOAc and concentrated at vacuum to remove the organic solvents. The residue was extracted twice with 20 ml of EtOAc and the both organic layers were combined and washed with 20 ml of demineralized water. Then, the layers were separated again and the organic one was concentrated at vacuum. In order to dry it properly, the residual oil was twice solved in 10 ml of EtOAc and concentrated at vacuum. The resulting crude, 5.54 g of a yellowish solid, contained Bimatoprost as main product. The crude was purified by flash chromatography on silica using a 8:2 Heptane:Acetone mixture as eluent affording 5.36 g (90.4% overall yield) of pure Bimatoprost as a white solid.

Example 7

Results of the amidation step in the process of the invention performed with compound of formula (III) wherein R$^1$ is butyl and R$^2$ is H (Example 4b carried out at the shown reaction temperature), compound of formula (III) wherein R$^1$ is ethyl and R$^2$ is H (Example 5b), and compound of formula (III) wherein R$^1$ and R$^2$ together are —CH$_2$—CH$_2$—CH$_2$— (Example 6b) at specific temperatures are shown in Table 1 below.

TABLE 1

| Ex. | Protection with | Reaction T (° C.) | Reaction time (h) | Acid impurity (%) |
| --- | --- | --- | --- | --- |
| 5b | Ethyl vinyl ether | 18/20 | 15/20 | 5.0/7.0 |
| 6b | 3,4-dihydropyrane | 18/20 | 19/24 | 2.0/3.0 |
| 4b | Butyl vinyl ether | 18/20 | 68/72 | 1.0/2.0 |
| 4b | Butyl vinyl ether | 26/28 | 48/52 | 3.0/4.0 |
| 4b | Butyl vinyl ether | 31/33 | 43/46 | 4.0/5.0 |

From the results above, it can be observed that the more bulky protecting group, the slower the reaction but the lower the presence of acidic impurity. The proper combination of the protecting group and the reaction temperature will allow obtaining an optimum relationship between the reaction time and the formation of the acid impurity.

By way of comparison, the amidation reaction over the trihydroxymethyl ester derivative disclosed in the prior art carried out at 18-20° C. takes about 72 hours, the final product having about 10% of bimatoprost free acid impurity.

Comparative Example 1

This comparative example illustrates the process disclosed in WO199406433.

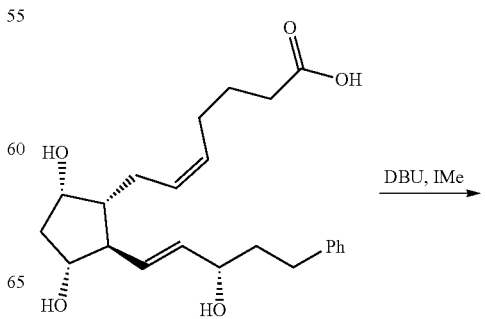

27
-continued

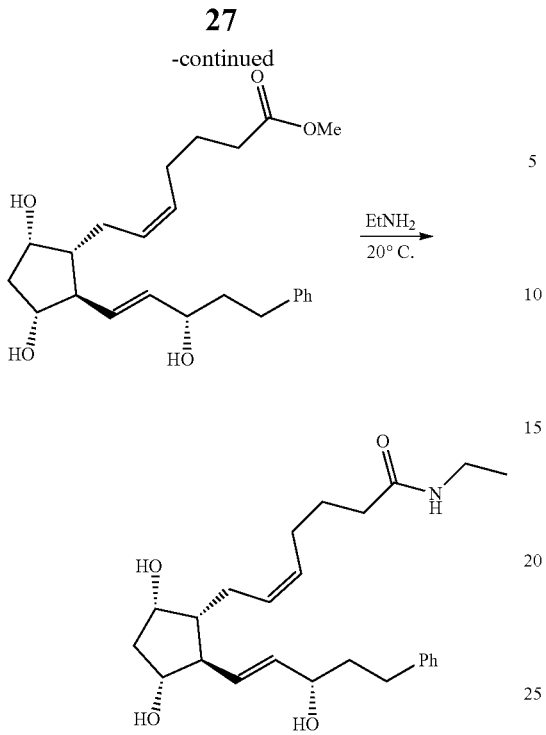

A mixture of acid bimatoprost (1.0 g 2.58 mmol), 1,8-diazabicyclo[5.4.0]undec-7-ene (DBU, 1.96 g, 12.88 mmol), methyl iodide (1.29 ml 12.88 mmol), and acetone (5.0 ml) was heated to reflux until the reaction was complete (after 2-3 hours). The end of the reaction was monitored TLC. Once the reaction was completed 10.0 ml of water were added and acetone was distilled off at vacuum. The product was extracted twice with 2×10.0 ml of EtOAc. The organic layers were combined and washed with 10.0 ml of a 0.5 M aqueous solution of hydrochloric acid and 10.0 with water. Then, the organic layer was concentrated at vacuum. In order to dry it properly, the residual oil was twice solved in 30 ml of EtOAc and concentrated at vacuum.

The resulting crude (1.05 g) was solved without further purification in 10.0 ml a 70.0% aqueous solution of $EtNH_2$ and the solution was stirred at 20-25° C. for 2-3 days until the reaction was complete. The completion of the reaction was checked by TLC. A reaction crude containing about 10.0% by weight of acid bimatoprost (depending on the reaction temperature) was obtained. After extracting the product with 10.0 ml of toluene, Then, the obtained organic phase is washed with water until the washing water is substantially neutral, and then, it was concentrated at vacuum to obtain crude bimatoprost (0.82 g to 0.92) g with a overall yield from 76.5% to 85.5% calculated from acid bimatoprost.

REFERENCES CITED IN THE APPLICATION

1. WO9406433
2. WO02096868
3. WO20100109476

28

The invention claimed is:

1. A process for the preparation of a compound of formula (I)

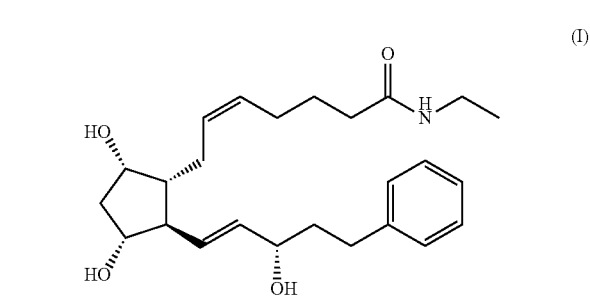 [SMILES: CCNC(=O)CCC/C=C\C[C@@H]1[C@@H](/C=C/[C@@H](O)CCc2ccccc2)[C@H](O)C[C@@H]1O]

which is bimatoprost, which comprises the following steps:

a) reacting a compound of formula (III):

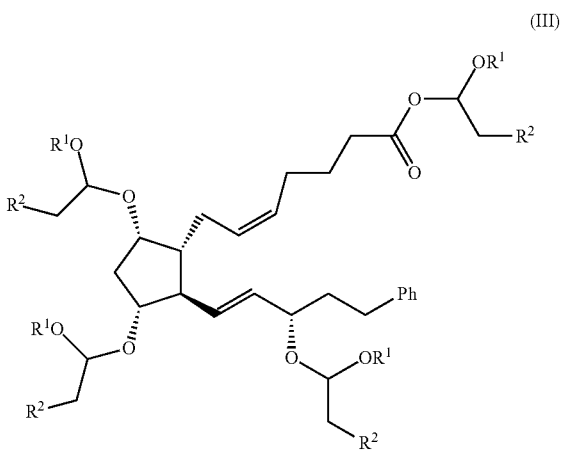

with ethylamine in the presence of a suitable solvent in order to obtain a compound of formula (II)

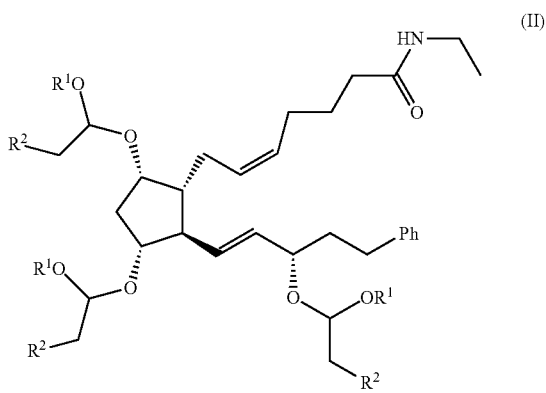

and, b) deprotecting compound of formula (II) to yield bimatoprost, wherein $R^1$ is selected from the group consisting of $(C_1-C_{16})$alkyl, $(C_1-C_{16})$haloalkyl, $(C_2-C_{16})$alkenyl, $(C_2-C_{16})$haloalkenyl, $(C_1-C_{16})$alkoxy$(C_1-C_{16})$alkyl, aryl, $(C_1-C_{16})$alkylaryl, allyl, —(CH$_2$—CH$_2$—O)$_n$—CH$_3$ wherein n=1, 2, 3 or 4, and —CH(O—CH$_2$—CH$_2$)$_2$, R$^2$ is selected from the group consisting of H, (C$_1$-C$_{16}$)alkyl, (C$_1$-C$_{16}$)haloalkyl, (C$_2$-C$_{16}$)alkenyl, (C$_2$-C$_{16}$)haloalkenyl, (C$_1$-C$_{16}$)alkoxy(C$_1$-C$_{16}$)alkyl, aryl, (C$_1$-C$_{16}$)alkylaryl, allyl, or, alternatively, R$^1$ and R$^2$ taken together are selected from the group consisting of —CH$_2$—CH$_2$—CH$_2$—, —CH$_2$—CH$_2$—, —O—CH$_2$—CH$_2$—, and —O—CH=CH.

2. The process according to claim 1, wherein R$^1$ is a (C$_1$-C$_4$)alkyl and R$^2$ is H.

3. The process according to claim 2, wherein R$^1$ is selected from ethyl and n-butyl and R$^2$ is H.

4. The process according to claim 1, wherein R$^1$ and R$^2$ taken together are selected from the group consisting of —CH$_2$—CH$_2$—CH$_2$—, —CH$_2$—CH$_2$—, —O—CH$_2$—CH$_2$—, and —O—CH=CH—.

5. The process according to claim 4, wherein R$^1$ and R$^2$ taken together are —CH$_2$—CH$_2$—CH$_2$—.

6. The process according to claim 1, wherein step a) is carried out at a temperature from 0 to 100° C.

7. The process according to claim 1, further comprising a previous step to prepare a compound of formula (III)

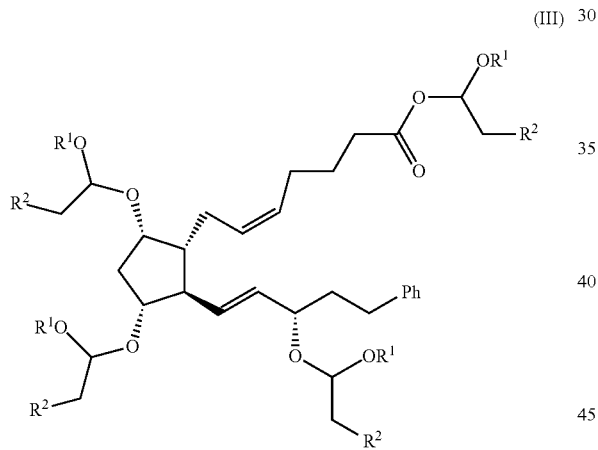

(III)

comprising reacting a compound of formula (V)

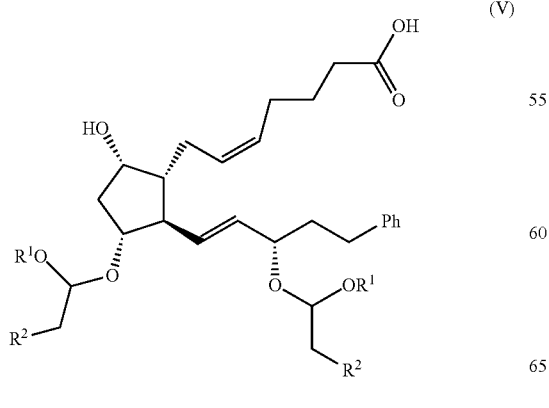

(V)

with a vinyl ether of formula (IV)

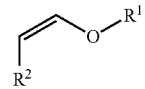

(IV)

wherein R$^1$ and R$^2$ are as defined in claim 1, in the presence of an acid catalyst.

8. A compound of formula (III):

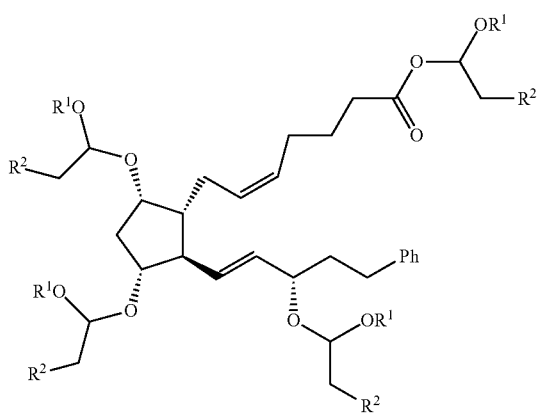

(III)

wherein

R$^1$ is selected from the group consisting of (C$_1$-C$_{16}$)alkyl, (C$_1$-C$_{16}$)haloalkyl, (C$_2$-C$_{16}$)alkenyl, (C$_2$-C$_{16}$)haloalkenyl, (C$_1$-C$_{16}$)alkoxy(C$_1$-C$_{16}$)alkyl, aryl, (C$_1$-C$_{16}$)alkylaryl, allyl, —(CH$_2$—CH$_2$—O)$_n$—CH$_3$ wherein n=1, 2, 3 or 4, and —CH(O—CH$_2$—CH$_2$)$_2$, R$^2$ is selected from the group consisting of H, (C$_1$-C$_{16}$)alkyl, (C$_1$-C$_{16}$)haloalkyl, (C$_2$-C$_{16}$)alkenyl, (C$_2$-C$_{16}$)haloalkenyl, (C$_1$-C$_{16}$)alkoxy(C$_1$-C$_{16}$)alkyl, aryl, (C$_1$-C$_{16}$)alkylaryl, allyl, or, alternatively, R$^1$ and R$^2$ taken together are selected from the group consisting of —CH$_2$—CH$_2$—CH$_2$—, —CH$_2$—CH$_2$—, —O—CH$_2$—CH$_2$—, and —O—CH=CH—.

9. The compound according to claim 8, wherein R$^1$ is a (C$_1$-C$_4$)alkyl and R$^2$ is H; or, alternatively, R$^1$ and R$^2$ taken together are selected from the group consisting of —CH$_2$—CH$_2$—CH$_2$—, —CH$_2$—CH$_2$—, —O—CH$_2$—CH$_2$—, and —O—CH=CH—.

10. The compound according to claim 9, wherein R$^1$ is selected from ethyl and n-butyl and R$^2$ is H; or, alternatively, R$^1$ and R$^2$ together are —CH$_2$—CH$_2$—CH$_2$—.

11. A process for the preparation of the compound of formula (III) as defined in claim 8, the process comprising reacting a compound of formula (V)

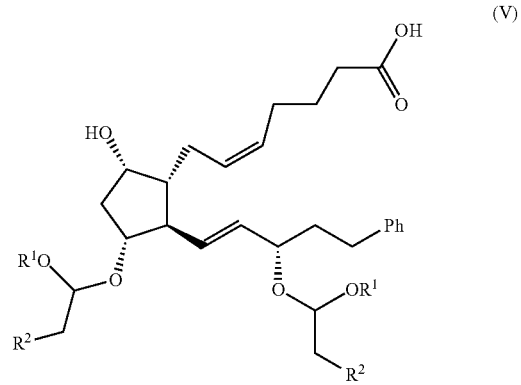

(V)

with a vinyl ether of formula (IV)

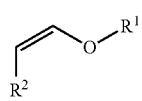

wherein $R^1$ and $R^2$ are as defined in claim 8, in the presence of an acid catalyst.

12. A compound of formula (II)

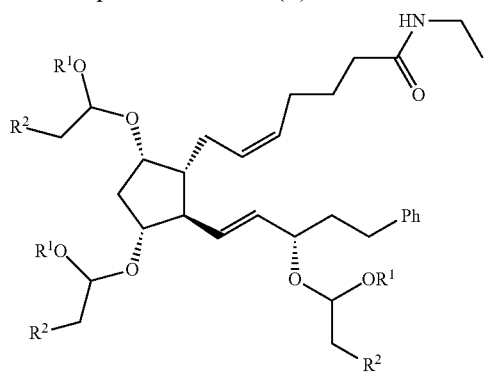

wherein
- $R^1$ is selected from the group consisting of $(C_1-C_{16})$alkyl, $(C_1-C_{16})$haloalkyl, $(C_2-C_{16})$alkenyl, $(C_2-C_{16})$haloalkenyl, $(C_1-C_{16})$alkoxy$(C_1-C_{16})$alkyl, aryl, $(C_1-C_{16})$alkylaryl, allyl, —$(CH_2$—$CH_2$—$O)_n$—$CH_3$ wherein n=1, 2, 3 or 4, and —$CH(O$—$CH_2$—$CH_2)_2$,
- $R^2$ is selected from the group consisting of H, $(C_1-C_{16})$alkyl, $(C_1-C_{16})$haloalkyl, $(C_2-C_{16})$alkenyl, $(C_2-C_{16})$haloalkenyl, $(C_1-C_{16})$alkoxy$(C_1-C_{16})$alkyl, aryl, $(C_1-C_{16})$alkylaryl, allyl,
- or, alternatively, $R^1$ and $R^2$ taken together are selected from the group consisting of —$CH_2$—$CH_2$—, —O—$CH_2$—$CH_2$—, and —O—CH=CH—.

13. The compound according to claim 12, wherein $R^1$ is a $(C_1-C_4)$alkyl and $R^2$ is H; or, alternatively, $R^1$ and $R^2$ together are selected from the group consisting of —$CH_2$—$CH_2$—, —O—$CH_2$—$CH_2$—, and —O—CH=CH—.

14. The compound according to claim 13, wherein $R^1$ is selected from ethyl and n-butyl and $R^2$ is H.

15. A process for the preparation of the compound of formula (II)

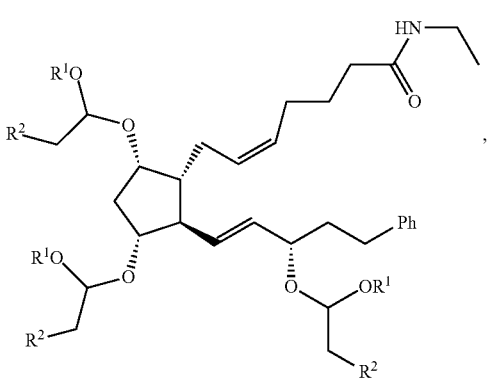

the process comprising reacting a compound of formula (III):

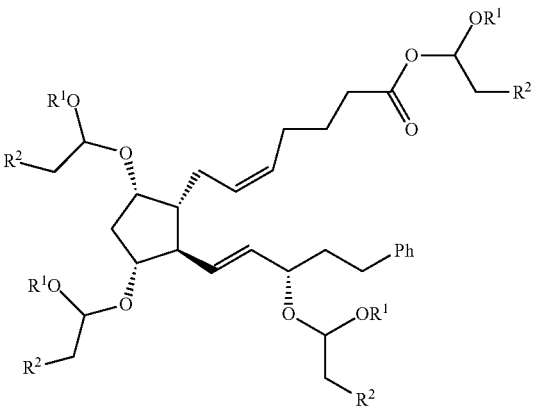

with ethylamine in the presence of a suitable solvent, wherein
- $R^1$ is selected from the group consisting of $(C_1-C_{16})$alkyl, $(C_1-C_{16})$haloalkyl, $(C_2-C_{16})$alkenyl, $(C_2-C_{16})$haloalkenyl, $(C_1-C_{16})$alkoxy$(C_1-C_{16})$alkyl, aryl, $(C_1-C_{16})$alkylaryl, allyl, —$(CH_2$—$CH_2$—$O)_n$—$CH_3$ wherein n=1, 2, 3 or 4, and —$CH(O$—$CH_2$—$CH_2)_2$,
- $R^2$ is selected from the group consisting of H, $(C_1-C_{16})$alkyl, $(C_1-C_{16})$haloalkyl, $(C_2-C_{16})$alkenyl, $(C_2-C_{16})$haloalkenyl, $(C_1-C_{16})$alkoxy$(C_1-C_{16})$alkyl, aryl, $(C_1-C_{16})$alkylaryl, allyl,
- or, alternatively, $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—.

16. The process according to claim 7, wherein $R^1$ is a $(C_1-C_4)$alkyl and $R^2$ is H.

17. The process according to claim 7, wherein $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—.

18. The process according to claim 11, wherein $R^1$ is a $(C_1-C_4)$alkyl and
$R^2$ is H; or, alternatively, $R^1$ and $R^2$ taken together are selected from the group consisting of —$CH_2$—$CH_2$—$CH_2$—, —$CH_2$—$CH_2$—, —O—$CH_2$—$CH_2$—, and —O—CH=CH—.

19. The process according to claim 11, wherein $R^1$ is selected from ethyl and n-butyl and $R^2$ is H; or, alternatively, $R^1$ and $R^2$ together are —$CH_2$—$CH_2$—$CH_2$—.

20. The process according to claim 15, wherein $R^1$ is a $(C_1-C_4)$alkyl and $R^2$ is H.

\* \* \* \* \*